United States Patent [19]

Lunkenheimer et al.

[11] Patent Number: 4,945,111

[45] Date of Patent: Jul. 31, 1990

[54] FUNGICIDAL N,N'-DIACYLAMINALS

[75] Inventors: Winfried Lunkenheimer; Dieter Berg, both of Wuppertal; Wilhelm Brandes, Leichlingen, all of Fed. Rep. of Germany

[73] Assignee: Bayer Aktiengesellschaft, Leverkusen, Fed. Rep. of Germany

[21] Appl. No.: 231,121

[22] Filed: Aug. 11, 1988

[30] Foreign Application Priority Data

Aug. 25, 1987 [DE] Fed. Rep. of Germany ....... 3728277

[51] Int. Cl.$^5$ ..................... A01N 37/34; C07C 255/64
[52] U.S. Cl. ..................... 514/521; 514/528; 514/482; 544/163; 546/305; 546/306; 546/323; 548/248; 548/536; 548/262.8; 549/76; 549/491; 549/496; 558/234; 558/237; 558/238; 558/301
[58] Field of Search ............... 558/301, 234, 237, 238; 514/521, 528

[56] References Cited

U.S. PATENT DOCUMENTS

| | | | |
|---|---|---|---|
| 3,984,568 | 10/1976 | Klopping ........................ | 558/301 X |
| 4,079,147 | 3/1978 | Brandes et al. ................. | 558/301 X |
| 4,178,383 | 12/1979 | Brandes et al. ................. | 558/301 X |
| 4,188,401 | 2/1980 | Brandes et al. ................. | 558/301 X |
| 4,478,848 | 10/1984 | Brandes et al. ................. | 558/301 X |

FOREIGN PATENT DOCUMENTS

| | | |
|---|---|---|
| 0206004 | 12/1986 | European Pat. Off. . |
| 3625460 | 2/1988 | Fed. Rep. of Germany ...... 558/301 |
| 3625497 | 2/1988 | Fed. Rep. of Germany ...... 558/301 |
| 3702283 | 8/1988 | Fed. Rep. of Germany ...... 558/301 |

*Primary Examiner*—Joseph Paul Brust
*Attorney, Agent, or Firm*—Sprung Horn Kramer & Woods

[57] ABSTRACT

Fungicidal N,N'-diacylaminals of the formula

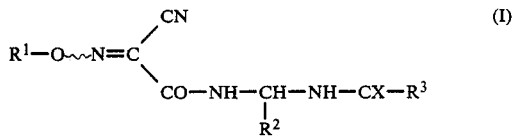

in which
  $R^1$ is optionally substituted alkyl, alkenyl, alkinyl, cycloalkyl or cycloalkenyl,
  $R^2$ and $R^3$ are hydrogen or various organic radicals, and
  X is oxygen or sulphur.

14 Claims, No Drawings

FUNGICIDAL N,N'-DIACYLAMINALS

The present invention relates to new N,N'-diacylaminals, several processes for their preparation, and their use in pesticides, in particular as fungicides.

It has already been disclosed that certain substituted 2-cyano-2-oximino-acetamides have a good fungicidal activity (cf., for example, EP-OS (European Published Specification) 0,201,999 and DE-OS (German Published Specification) 3,602,243). However, the action of these compounds is not always fully satisfactory, in particular at low application rates and concentrations.

New N,N'-diacylaminals of the general formula (I)

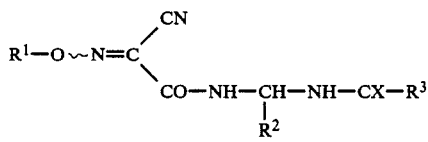

in which
- $R^1$ stands for optionally substituted alkyl having the following substituents: halogen, cyano, $-COOR^I$, $-CONR^{II}R^{III}$, $-OR^{IV}$, acyl, optionally substituted aryl, optionally substituted cycloalkyl or optionally substituted heterocyclyl; $R^1$ furthermore stands for in each case optionally substituted alkenyl or alkinyl, or for in each case optionally substituted cycloalkyl or cycloalkenyl,
- $R^2$ stands for hydrogen or for optionally substituted alkyl having the following substituents: cyano, alkoxy, alkylthio, $-COOR^I$, acylamino, optionally substituted aryl, optionally substituted cycloalkyl or optionally substituted heterocyclyl; $R^2$ furthermore stands for in each case optionally substituted alkenyl or alkinyl, for in each case optionally substituted cycloalkyl or cycloalkenyl, for optionally substituted aryl or for optionally substituted heterocyclyl,
- $R^3$ stands for hydrogen or for optionally substituted alkyl having the following substituents: halogen, alkoxy, alkylthio, alkylsulphinyl, alkylsulphonyl, acyloxy, acylamino, cyano, $-COOR^I$, optionally substituted aryl, optionally substituted cycloalkyl or optionally substituted heterocyclyl; $R^3$ furthermore stands for in each case optionally substituted alkenyl or alkinyl; $R^3$ additionally stands for in each case optionally bridged and/or fused, in each case optionally substituted cycloalkyl or cycloalkenyl; $R^3$ in addition stands for optionally fused, optionally substituted aryl or optionally fused, optionally substituted heterocyclyl, or furthermore for alkoxycarbonyl, $-OR^4$, $-SR^4$ or $-NR^5R^6$, stands for optionally substituted alkyl having the following substituents: halogen, $-OR^{IV}$, $-SR^{IV}$, $-COOR^I$, $-CONR^{II}R^{III}$, $-CN$, $-NR^{II}R^{III}$, acyl, in each case optionally substituted aryl or aryloxy, in each case optionally substituted cycloalkyl or cycloalkenyl, or optionally substituted heterocyclyl; $R^4$ furthermore stands for in each case optionally substituted alkenyl or alkinyl, or furthermore for in each case optionally substituted cycloalkyl or cycloalkenyl,
- $R^5$ stands for hydrogen or for optionally substituted alkyl having the following substituents: halogen, cyano, $-COOR^I$, $-CONR^{II}R^{III}$, $-NR^{II}R^{III}$, $-OR^{IV}$, $-S(O)_nR^{IV}$, acyl, or in each case optionally substituted aryl, heterocyclyl, cycloalkyl or cycloalkenyl; $R^5$ furthermore stands for in each case optionally substituted alkenyl, alkinyl, cycloalkyl, cycloalkenyl, aryl or heterocyclyl, and
- $R^6$ stands for hydrogen or for optionally substituted alkyl having the following substituents: halogen, cyano, $-COOR^I$, $-CONR^{II}R^{III}$, $-NR^{II}R^{III}$, $-OR^{IV}$, $-S(O)_nR^{IV}$, acyl, or in each case optionally substituted aryl, heterocyclyl, cycloalkyl or cycloalkenyl; or $R^6$ furthermore stands for in each case optionally substituted alkenyl, alkinyl, cycloalkyl, cycloalkenyl, aryl, heterocyclyl or the $-OR^{IV}$ group, or
- $R^5$ and $R^6$, together with the nitrogen atom to which they are bonded, stand for an optionally substituted heterocyclic ring which may contain further hetero atoms,
- $R^I$ stands for hydrogen or optionally substituted alkyl having the following substituents: halogen, or in each case optionally substituted aryl, cycloalkyl or cycloalkenyl,
- $R^{II}$ and $R^{III}$ are identical or different and stand for hydrogen or optionally substituted alkyl having the following substituents: halogen, $-COOR^{IV}$, $-CONR^IR^{IV}$, or in each case optionally substituted aryl, cycloalkyl or cycloalkenyl; or $R^{II}$ and $R^{III}$ furthermore stand for alkenyl, alkinyl, or in each case optionally substituted cycloalkyl, cycloalkenyl, aryl or heterocyclyl, or, together with the nitrogen atom to which they are bonded, stand for an optionally substituted heterocyclic ring which may contain further hetero atoms,
- $R^{IV}$ stands for hydrogen, alkyl, aralkyl or acyl,
- n stands for the numbers 0, 1 or 2, and
- X stands for oxygen or sulphur, have now been found.

The compounds of the formula (I) can exist in various geometrical isomers, depending on the arrangement of the substituents on the C=N group (E- or Z-isomers).

The compounds may have one or more asymmeytrical carbon atoms; they can thus also exist as enantiomers or diastereomers, which can be produced in various amount ratios. They are predominantly produced as racemates.

It has furthermore been found that the new N,N'-diacylaminals of the general formula (I)

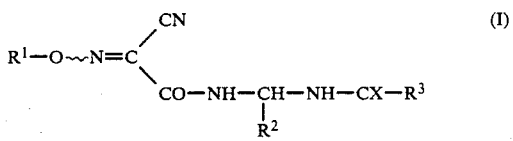

in which
- $R^1$ stands for optionally substituted alkyl having the following substituents: halogen, cyano, $-COOR^I$, $-CONR^{II}R^{III}$, $-OR^{IV}$, acyl, optionally substituted aryl, optionally substituted cycloalkyl or optionally substituted heterocyclyl; $R^1$ furthermore stands for in each case optionally substituted alkenyl or alkinyl, or for in each case optionally substituted cycloalkyl or cycloalkenyl,
- $R^2$ stands for hydrogen or for optionally substituted alkyl having the following substituents: cyano, alkoxy, alkylthio, $-COOR^I$, acylamino, optionally substituted aryl, optionally substituted cycloalkyl or optionally substituted heterocyclyl; $R^2$ furthermore stands for in each case optionally substituted alkenyl or alkinyl, for in each case optionally substituted cycloalkyl or cycloalkenyl, for optionally substituted aryl or for optionally substituted heterocyclyl, $R^3$ stands for hydrogen or for optionally substituted alkyl having the following substituents: halogen, alkoxy, alkylthio, alkylsulphinyl, alkylsulphonyl, acyloxy, acylamino, cyano, —COOR$^I$, optionally substituted aryl, optionally substituted cycloalkyl or optionally substituted heterocyclyl; $R^3$ furthermore stands for in each case optionally substituted alkenyl or alkinyl; $R^3$ additionally stands for in each case optionally bridged and/or fused, in each case optionally substituted cycloalkyl or cycloalkenyl; $R^3$ in addition stands for optionally fused, optionally substituted aryl or optionally fused, optionally substituted heterocyclyl, or furthermore for alkoxycarbonyl, —OR$^4$, —SR$^4$ or —NR$^5$R$^6$, $R^4$ stands for optionally substituted alkyl having the following substituents: halogen, —OR$^{IV}$, —SR$^{IV}$, —COOR$^I$, —CONR$^{II}$R$^{III}$, —CN, —NR$^{II}$R$^{III}$, acyl, in each case optionally substituted aryl or aryloxy, in each case optionally substituted cycloalkyl or cycloalkenyl, or optionally substituted heterocyclyl; $R^4$ furthermore stands for in each case optionally substituted alkenyl or alkinyl, or furthermore for in each case optionally substituted cycloalkyl or cycloalkenyl, $R^5$ stands for hydrogen or for optionally substituted alkyl having the following substituents: halogen, cyano, —COOR$^I$, —CONR$^{II}$R$^{III}$, —NR$^{II}$R$^{III}$, —OR$^{IV}$, —S(O)$_n$R$^{IV}$, acyl, or in each case optionally substituted aryl, heterocyclyl, cycloalkyl or cycloalkenyl; $R^5$ furthermore stands for in each case optionally substituted alkenyl, alkinyl, cycloalkyl, cycloalkenyl, aryl or heterocyclyl, and $R^6$ stands for hydrogen or for optionally substituted alkyl having the following substituents: halogen, cyano, —COOR$^I$, —CONR$^{II}$R$^{III}$, —NR$^{II}$R$^{III}$, —OR$^{IV}$, —S(O)$_n$R$^{IV}$, acyl, or in each case optionally substituted aryl, heterocyclyl, cycloalkyl or cycloalkenyl; or $R^6$ furthermore stands for in each case optionally substituted alkenyl, alkinyl, cycloalkyl, cycloalkenyl, aryl or heterocyclyl or the —OR$^{IV}$ group, $R^5$ and $R^6$, together with the nitrogen atom to which they are bonded, stand for an optionally substituted heterocyclic ring which may contain further hetero atoms, $R^I$ stands for hydrogen or optionally substituted alkyl having the following substituents: halogen, or in each case optionally substituted aryl, cycloalkyl or cycloalkenyl, $R^{II}$ and $R^{III}$ are identical or different and stand for hydrogen or optionally substituted alkyl having the following substituents: halogen, —COOR$^{IV}$, —CONR$^I$R$^{IV}$, or in each case optionally substituted aryl, cycloalkyl or cycloalkenyl; or $R^{II}$ and $R^{III}$ furthermore stand for alkenyl, alkinyl, or in each case optionally substituted cycloalkyl, cycloalkenyl, aryl or heterocyclyl, or, together with the nitrogen atom to which they are bonded, stand for an optionally substituted heterocyclic ring which may contain further hetero atoms, $R^{IV}$ stands for hydrogen, alkyl, aralkyl or acyl, n stands for the numbers 0, 1 or 2, and X stands for oxygen or sulphur, are obtained when (a) N-(2-cyano-2-oximino-acetyl)-aminals of the formula (II)

$$R^1-O-N=C\begin{matrix}CN\\ \\ CO-NH-CH-NH_2\\ |\\ R^2\end{matrix} \times HY \quad (II)$$

in which $R^1$ and $R^2$ have the abovementioned meaning, and HY stands for the equivalent of an inorganic or organic acid, are reacted with an acylating reagent of the formula (IIIa) or (IIIb)

$$Z-CX-R^3 \quad (IIIa)$$

or $$X=C=N-R^6 \quad (IIIb)$$

in which

Z stands for a customary leaving group, such as halogen, —O—CO—R$^3$, —O—CO—OR$^4$, —OR$^4$, —SR$^4$, carboxymethoxy or carboxymethylthio, and $R^3$, $R^4$, $R^6$ and X have the abovementioned meaning, if appropriate in the presence of a base and in the presence of a diluent and if appropriate in the presence of a catalyst;

or (b) isocyanates of the formula (IV)

$$R^1-O-N=C\begin{matrix}CN\\ \\ CO-NH-CH-N=C=O\\ |\\ R^2\end{matrix} \quad (IV)$$

in which $R^1$ and $R^2$ have the abovementioned meaning, are reacted with a protic nucleophile of the formula (Va) or (Vb)

$$HO-CO-R^3 \quad (Va)$$

or $$H-R^7 \quad (Vb)$$

in which $R^7$ stands for —OR$^4$, —SR$^4$ or —NR$^5$R$^6$, and $R^3$, $R^4$, $R^5$ and $R^6$ have the abovementioned meaning, in the presence of a diluent and if appropriate in the presence of a catalyst.

Finally, it has been found that the new N,N'-diacylaminals have strong fungicidal properites, inter alia. In this respect, the compounds according to the invention surprisingly exhibit a stronger action than the substituted 2-cyano-2-oximino-acetamides known from the prior art, which are similar compounds constitutionally or regarding their action. The substances according to the invention thus represent an enrichment of the art.

In the text below, all aliphatic radicals, such as alkyl, alkoxy, alkenyl, etc., alone or in combinations, such as alkoxyalkyl, may be straight-chain or branched, and in addition the aliphatic radicals may generally be substituted by identical or different substituents, preferably monosubstituted to pentasubstituted, particularly preferably monosubstituted, disubstituted or trisubstituted, or very particularly preferably monosubstituted or disubstituted; likewise, all ring systems are optionally monosubstituted to pentasubstituted by identical or different substituents, particularly preferably monosubstituted, disubstituted or trisubstituted, or very particularly preferably monosubstituted or disubstituted, unless otherwise stated or not expressly described.

Formula (I) provides a general definition of the N,N'-diacylaminals according to the invention. In this formula (I), $R^1$ preferably stands for straight-chain or branched alkyl having 1 to 6 carbon atoms which is optionally monosubstituted to pentasubstituted by identical or different substituents, the following substituents being suitable: fluorine, chlorine, bromine, iodine, cyano, —$COOR^I$, —$CONR^{II}R^{III}$, —$OR^{IV}$, acyl having 2 to 9 carbon atoms, phenyl which is optionally monosubstituted to pentasubstituted by identical or different substituents, phenyl substituents which may be mentioned being: halogen, alkyl and alkoxy each having 1 to 4 carbon atoms, halogenoalkyl and halogenoalkoxy each having 1 to 2 carbon atoms and 1 to 5 identical or different halogen atoms; further alkyl substituents are cycloalkyl having 3 to 6 carbon atoms which is optionally monosubstituted to pentasubstituted by identical or different alkyl having 1 to 4 carbon atoms, and 3- to 6-membered heterocyclyl having 1 to 3 identical or different hetero atoms, such as nitrogen, oxygen and sulphur atoms, which is optionally monosubstituted to pentasubstituted by identical or different substituents from the series comprising halogen and alkyl having 1 to 4 carbon atoms; $R^1$ furthermore preferably stands for straight-chain or branched alkenyl or alkinyl, each of which has 2 to 6 carbon atoms and is optionally monosubstituted, disubstituted or trisubstituted by identical or different substituents, substituents which may be mentioned being: phenyl which is optionally monosubstituted to pentasubstituted by identical or different substituents from the series comprising halogen and alkyl having 1 to 4 carbon atoms; $R^1$ in addition preferably stands for cycloalkyl having 3 to 6 carbon atoms or cycloalkenyl having 5 to 7 carbon atoms, each of which is optionally monosubstituted to pentasubstituted by identical or different alkyl having 1 to 4 carbon atoms;

$R^2$ preferably stands for hydrogen or straight-chain or branched alkyl having 1 to 6 carbon atoms which is optionally monosubstituted to pentasubstituted by identical or different substituents, suitable being the following: cyano, alkoxy and alkylthio, each having 1 to 4 carbon atoms, —$COOR^I$, acylamino having 2 to 9 carbon atoms, phenyl which is optionally monosubstituted to pentasubstituted by identical or different substituents, suitable substituents being the phenyl substituents mentioned above as preferred in the case of $R^1$; further alkyl substituents are cycloalkyl having 3 to 6 carbon atoms which is optionally monosubstituted to pentasubstituted by identical or different alkyl having 1 to 4 carbon atoms, and 3- to 6-membered heterocyclyl having 1 to 3 identical or different hetero atoms, such as nitrogen, oxygen and sulphur atoms, which is optionally monosubstituted to pentasubstituted by identical or different substituents from the series comprising halogen and alkyl having 1 to 4 carbon atoms; $R^2$ furthermore preferably stands for straight-chain or branched alkenyl or alkinyl, each of which has to 6 carbon atoms and is optionally monosubstituted, disubstituted or trisubstituted by identical or different substituents, substituents which may be mentioned being: phenyl which is optionally monosubstituted to pentasubstituted by identical or different substituents from the series comprising halogen and alkyl having 1 to 4 carbon atoms; $R^2$ in addition preferably stands for cycloalkyl having 3 to 6 carbon atoms or cycloalkenyl having 5 to 7 carbon atoms, each of which is optionally monosubstituted to pentasubstituted by identical or different alkyl having 1 to 4 carbon atoms; $R^2$ additionally preferably stands for phenyl which is optionally monosubstituted to pentasubstituted by identical or different substituents, suitable substituents being the phenyl substituents mentioned above as preferred in the case of $R^1$; $R^2$ furthermore preferably stands for 3- or 6-membered heterocyclyl having 1 to 3 identical or different hetero atoms, such as nitrogen, oxygen and sulphur atoms, which is optionally monosubstituted to pentasubstituted by identical or different substituents from the series comprising halogen and alkyl having 1 to 4 carbon atoms;

$R^3$ preferably represents hydrogen or straight-chain or branched alkyl having 1 to 6 carbon atoms which is optionally monosubstituted to pentasubstituted by identical or different substituents, suitable substituents being the following: fluorine, chlorine, bromine, iodine, cyano, alkoxy, alkylthio, alkylsulphinyl and alkylsulphonyl each having 1 to 4 carbon atoms, acyloxy and acylamino each having 2 to 9 carbon atoms, —$COOR^I$, phenyl which is optionally monosubstituted to pentasubstituted by identical or different substituents, suitable substituents being the phenyl substituents mentioned above as preferred in the case of $R^1$; further alkyl substituents are cycloalkyl having 3 to 6 carbon atoms which is optionally monosubstituted to pentasubstituted by identical or different alkyl having 1 to 4 carbon atoms, and 3- to 6-membered heterocyclyl having 1 to 3 identical or different hetero atoms, such as nitrogen, oxygen and sulphur atoms, which is optionally monosubstituted to pentasubstituted by identical or different substituents from the series comprising halogen and alkyl having 1 to 4 carbon atoms; $R^3$ furthermore preferably stands for straight-chain or branched alkenyl or alkinyl, each of which has 2 to 6 carbon atoms and is optionally monosubstituted, disubstituted or trisubstituted by identical or different substituents, substituents which may be mentioned being: phenyl which is optionally monosubstituted to pentasubstituted by identical or different substituents from the series comprising halogen and alkyl having 1 to 4 carbon atoms; $R^3$ furthermore preferably stands for cycloalkyl having 3 to 6 carbon atoms or cycloalkenyl having 5 to 7 carbon atoms, each of which is optionally bridged by methylene or ethylene and/or fused to 1 or 2 benzene, cyclopentane or cyclohexane rings and is optionally monosubstituted to pentasubstituted by identical or different substituents, substituents which may be mentioned being: halogen, alkyl and alkoxy each having 1 to 4 carbon atoms, acyloxy and acylamino each having 2 to 5 carbon atoms, the oxo group, phenyl, hydroxycarbonyl and alkoxycarbonyl having 1 to 4 carbon atoms in the alkoxy part; $R^3$ in addition preferably stands for phenyl which is optionally fused to 1 or 2 benzene or cyclohexane rings and is optionally substituted or pentasubstituted by identical or different substituents, substituents which may be mentioned being: halogen, hydroxyl, nitro, alkyl and alkoxy each having 1 to 4 carbon atoms, halogenalkyl and halogenoalkoxy each having 1 or 2 carbon atoms and 2 to 5 identical or different halogen atoms, such as fluorine and chlorine atoms, acylamino and acylalkylamino each having 2 to 5 carbon atoms in the acyl part and 1 to 4 carbon atoms in the alkyl part, hydroxycarbonyl and alkoxycarbonyl having 1 to 4 carbon atoms in the alkoxy part;

$R^3$ furthermore preferably stands for 5- or 6-membered heterocyclyl having 1 to 3 identical or different hetero atoms, such as nitrogen, oxygen and sulphur atoms, which is optionally fused to 1 or 2 benzene, cyclopentane or cyclohexane rings and is optionally monosubstituted to pentasubstituted by identical or different substituents, substituents which may be mentioned being: halogen, alkyl having 1 to 4 carbon atoms, acyl having 2 to 9 carbon atoms, phenyl, the oxo group and hydroxyl; finally, $R^3$ alternatively preferably stands for alkoxycarbonyl having 1 to 4 carbon atoms in the alkoxy part, or for —$OR^4$, —$SR^4$ or —$NR^5R^6$;

$R^4$ preferably stands for straight-chain or branched alkyl having 1 to 6 carbon atoms which is optionally monosubstituted to pentasubstituted by identical or different substituents, suitable substituents being the following: halogen, —$OR^{IV}$, —$SR^{IV}$, —$COOR^I$, —$CONR^{II}R^{III}$, CN, —$NR^{II}R^{III}$, acryl having 2 to 9 carbon atoms, phenyl or phenoxy, each of which is optionally monosubstituted to pentasubstituted by identical or different substituents from the series comprising halogen and alkyl having 1 to 4 carbon atoms, cycloalkyl having 3 to 6 carbon atoms or cycloalkenyl having 5 to 7 carbon atoms, each of which is optionally monosubstituted to pentasubstituted by identical or different alkyl having 1 to 4 carbon atoms, and 3- to 6-membered heterocyclyl having 1 to 3 identical or different hetero atoms, such as nitrogen, oxygen and sulphur atoms, which is optionally monosubstituted or pentasubstituted by identical or different substituents from the series comprising halogen and alkyl having 1 to 4 carbon atoms; $R^4$ furthermore preferably stands for alkenyl or alkinyl each having 2 to 6 carbon atoms, or for cycloalkyl having 3 to 6 carbon atoms or cycloalkenyl having 5 to 7 carbon atoms, each of which is optionally monosubstituted to pentasubstituted by identical or different alkyl having 1 to 4 carbon atoms;

preferably stands for hydrogen or for straight-chain or branched alkyl having 1 to 4 carbon atoms which is optionally monosubstituted or disubstituted by identical or different substituents, substituents which may preferably be mentioned being: halogen, cyano, —$COOR^I$, —$CONR^{II}R^{III}$, —$NR^{II}R^{III}$, —$OR^{IV}$, —$S(O)_nR^{IV}$, acyl having 2 to 9 carbon atoms, phenyl which is optionally monosubstituted to pentasubstituted by identical or different substituents from the series comprising halogen and alkyl having 1 to 4 carbon atoms, a 5- or 6-membered heterocyclic ring having 1 to 3 identical or different hetero atoms, for example nitrogen, oxygen and sulphur, which is optionally monosubstituted or pentasubstituted by identical or different substituents from the series comprising halogen, alkyl and alkoxy each having 1 to 4 carbon atoms, or cycloalkyl having 3 to 6 carbon atoms or cycloalkenyl having 5 to 7 carbon atoms, each of which is optionally monosubstituted to pentasubstituted by identical or different alkyl having 1 to 4 carbon atoms; $R^5$ furthermore preferably stands for straight-chain or branched alkenyl or alkinyl each having 2 to 6 carbon atoms; for cycloalkenyl having 5 to 7 carbon atoms which is optionally monosubstituted or pentasubstituted by identical or different alkyl having 1 to 4 carbon atoms, or for cycloalkyl having 3 to 6 carbon atoms which is optionally monosubstituted to pentasubstituted by identical or different substituents, substituents which may preferably be mentioned being: halogen, alkyl and alkoxy each having 1 to 4 carbon atoms, cyano, amino, carbamoyl, alkylamino, dialkylamino, alkylcarbamoyl and dialkylcarbamoyl each having 1 to 4 carbon atoms in each alkyl part, alkoxycarbonylamino having 1 to 4 carbon atoms in the alkoxy part, cycloalkyl and cycloalkylalkyl having 5 or 6 carbon atoms in the cycloalkyl part and 1 to 4 carbon atoms in the straight-chain or branched alkyl part, or phenyl or pyrrolidone each of which is optionally monosubstituted to pentasubstituted by identical or different substituents from the series comprising halogen and alkyl having 1 to 4 carbon atoms; $R^5$ additionally preferably stands for phenyl which is optionally monosubstituted to pentasubstituted by identical or different substituents from the series comprising halogen, alkyl or alkoxy each having 1 to 4 carbon atoms, or halogenoalkyl or halogenoalkoxy each having 1 to 2 carbon atoms and 1 to 5 identical or different halogen atoms, or for a 5- or 6-membered heterocyclic ring having 1 to 3 identical or different hetero atoms, such as, in particular, nitrogen, oxygen and sulphur atoms, which is optionally monosubstituted to pentasubstituted by identical or different substituents; substituents which may be mentioned being halogen, mercapto, phenyl, straight-chain or branched alkyl, alkoxy, alkylthio, alkylsulphinyl and alkylsulphonyl having 1 to 4 carbon atoms in each alkyl part;

$R^6$ preferably stands for the meanings of $R^5$ or the —$OR^{IV}$ group;

or $R^5$ or $R^6$, together with the nitrogen atom to which they are bonded, preferably stand for a monocyclic, bicyclic or tricyclic heterocyclic ring or spiroheterocyclic ring having 1 to 3 further identical or different hetero atoms, such as oxygen, nitrogen or sulphur atoms, which is optionally monosubstituted to pentasubstituted by identical or different substituents, substituents which may be mentioned being:

straight-chain or branched alkyl or alkoxy each having 1 to 4 carbon atoms, cycloalkyl having 3 to 6 carbon atoms, the hydroxyl or the oxo group, straight-chain or branched alkenyl having 2 to 4 carbon atoms, hydroxycarbonyl, alkoxycarbonyl having 1 to 4 carbon atoms in the straight-chain or branched alkyl part, carbamoyl, alkylcarbamoyl or dialkylcarbamoyl each having 1 to 4 carbon atoms in the straight-chain or branched alkyl part, or phenyl or phenylalkyl which has 1 to 4 carbon atoms in the straight-chain or branched alkyl part and each of which is optionally monosubstituted or disubstituted by identical or different substituents from the series comprising halogen or straight-chain or branched alkyl or alkoxy each having 1 to 4 carbon atoms; preferably stands for hydrogen or straight-chain or branched alkyl having 1 to 6 carbon atoms, preferably stands for hydrogen, straight-chain or branched alkyl having 1 to 6 carbon atoms, phenylalkyl which has 1 to 4 carbon atoms in the straight-chain or branched alkyl part and is optionally monosubstituted to pentasubstituted by identical or different substituents, phenyl substituents which may be mentioned being: halogen, alkyl or alkoxy each having 1 to 4 carbon atoms, or halogenoalkyl or halogenoalkoxy each having 1 to 2 carbon atoms and 2 to 5 identical or different halogen atoms; $R^{II}$ furthermore stands for alkoxycarbonylalkyl, carbamoylalkyl, alkylcarbamoylalkyl or dialkylcarbamoylalkyl each having 1 to 4 carbon atoms in each alkyl part, or for cycloalkyl having 3 to 6 carbon atoms which is optionally substituted by straight-chain or branched alkyl having 1 to 4 carbon atoms, preferably stands for hydrogen, straight-chain or branched alkyl having 1 to 6 carbon atoms, phenylalkyl which has 1 to 4 carbon atoms in the straight-chain or branched alkyl part and is optionally monosubstituted to pentasubstituted by identical or different substituents, suitable phenyl substituents being the phenyl substituents mentioned as preferred in the case of $R^{II}$; $R^{III}$ furthermore stands for alkoxycarbonylalkyl, carbamoylalkyl, alkylcarbamoylalkyl or dialkylcarbamoylalkyl each having 1 to 4 carbon atoms in each alkyl part, or for cycloalkyl having 3 to 6 carbon atoms which is optionally substituted by straight-chain or branched alkyl having 1 to 4 carbon atoms;

$R^{IV}$ preferably stands for hydrogen, straight-chain or branched alkyl having 1 to 6 carbon atoms, phenylalkyl which has 1 to 4 carbon atoms in the straight-chain or branched alkyl part and is optionally monosubstituted to pentasubstituted by identical or different substituents, suitable phenyl substituents preferably being the phenyl substituents mentioned in the case of $R^{II}$; or $R^{IV}$ furthermore stands for acyl having 2 to 9 carbon atoms;

n preferably stands for the numbers 0, 1 or 2, and

X preferably stands for oxygen or sulphur.

Particularly preferred N,N'-diacylaminals are those of the general formula (I) in which $R^1$ stands for straight-chain or branched alkyl having 1 to 4 carbon atoms which is optionally monosubstituted, disubstituted or trisubstituted by identical or different substituents, suitable substituents being the following: fluorine, chlorine, bromine, iodine, cyano, —COOR$^I$, —CONR$^{II}$R$^{III}$, —OR$^{IV}$, acyl having 2 to 9 carbon atoms, phenyl which is optionally monosubstituted, disubstituted or trisubstituted by identical or different substituents from the series comprising fluorine, chlorine, methyl and methoxy, cyclopropyl or cyclohexyl, each of which is optionally monosubstituted, disubstituted or trisubstituted by methyl, or heterocyclic rings of the formulae

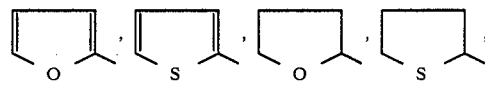

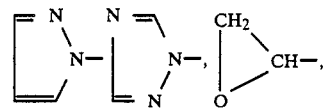

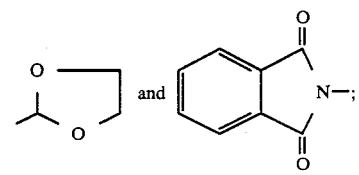

which are optionally monosubstituted, disubstituted or trisubstituted by identical or different alkyl having 1 or 2 carbon atoms;

$R^1$ furthermore stands for allkyl or propargyl, each of which is optionally monosubstituted or disubstituted by methyl, or for cyclopropyl, cyclohexyl, cyclopentyl or cyclohexenyl, each of which is optionally monosubstituted, disubstituted or trisubstituted by methyl;

$R^2$ stands for hydrogen or straight-chain or branched alkyl having 1 to 4 carbon atoms which is optionally monosubstituted, disubstituted or trisubstituted by identical or different substituents, suitable substituents being the following: cyano, methoxy, ethoxy, methylthio, ethylthio, —COOR$^I$, acylamino having 2 to 9 carbon atoms, phenyl which is optionally monosubstituted, disubstituted or trisubstituted by identical or different substituents from the series comprising halogen, methyl and methoxy, cyclopropyl or cyclohexyl, each of which is optionally monosubstituted, disubstituted or trisubstituted by methyl, or heterocyclic rings of the formulae

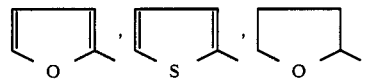

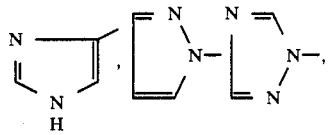

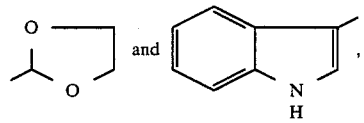

each of which is optionally monosubstituted, disubstituted or trisubstituted by identical or different alkyl having 1 or 2 carbon atoms;

R² furthermore stands for allyl, allenyl, vinyl, propargyl or ethinyl, each of which is optionally substituted by phenyl which may optionally be monosubstituted, disubstituted or trisubstituted by identical or different substituents from the series comprising halogen and methyl;

R² in addition stands for cyclopropyl, cyclohexyl, cyclopentenyl or cyclohexenyl; R² additionally stands for phenyl which is optionally monosubstituted, disubstituted or trisubstituted by identical or different substitents from the series comprising halogen, methyl and methoxy, or heterocyclic rings of the formulae

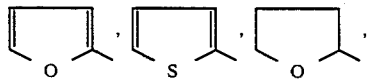

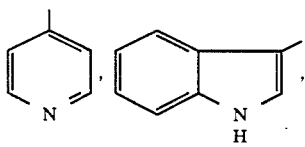

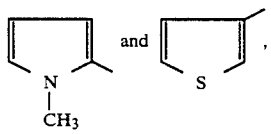

each of which is optionally monosubstituted, disubstituted or trisubstituted by identical or different alkyl having 1 to 2 carbon atoms;

R³ stands for hydrogen or straight-chain or branched alkyl having 1 to 4 carbon atoms which is optionally monosubstituted, disubstituted or trisubstituted by identical or different substituents, suitable substituents being the following: fluorine, chlorine, bromine, iodine, cyano, alkoxy, alkylthio, alkylsulphinyl and alkylsulphonyl each having 1 or 2 carbon atoms, acyloxy and acylamino each having 2 to 9 carbon atoms, —COOR$^I$, cyclopropyl, cyclopentyl, cyclohexyl or phenyl which is optionally monosubstituted, disubstituted or trisubstituted by identical or different substituents from the series comprising halogen and methyl, or heterocyclic rings of the formulae

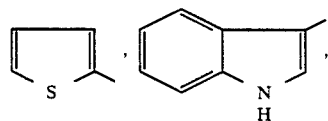

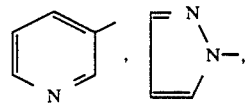

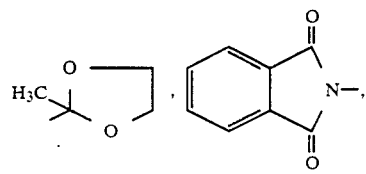

-continued

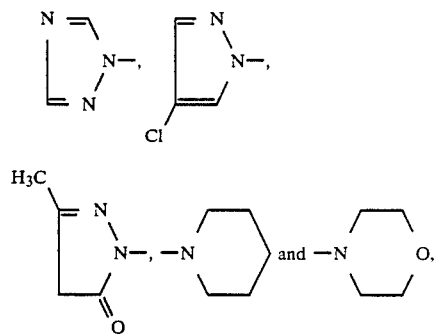

each of which is optionally monosubstituted, disubstituted or trisubstituted by identical or different alkyl having 1 or 2 carbon atoms; R³ furthermore stands for vinyl or ethinyl, each of which is optionally substituted by phenyl which may optionally be monosubstituted, disubstituted or trisubstituted by identical or different substituents from the series comprising halogen and methyl, or by methyl; R³ additionally stands for cyclopropyl, cyclopentyl, cyclohexyl, cyclopentenyl or cyclohexenyl, each of which is optionally bridged by methylene or ethylene and/or fused to 1 or 2 benzene, cyclopentane or cyclohexane rings and each of which is optionally monosubstituted, disubstituted or trisubstituted by identical or different substituents, substituents which may be mentioned being: halogen, methyl, methoxy, acyloxy and acylamino each having 2 to 5 carbon atoms, the oxo group, phenyl, hydroxycarbonyl, methoxycarbonyl and ethoxycarbonyl; R³ in addition stands for phenyl which is optionally fused to 1 or 2 benzene or cyclohexane rings and is optionally monosubstituted, disubstituted or trisubstituted by identical or different substituents, substituents which may be mentioned being: fluorine, chlorine, hydroxyl, nitro, methyl, methoxy, acylamino and N-alkyl-acyl-amino each having 2 to 5 carbon atoms in the acyl part and 1 or 2 carbon atoms in the alkyl part, hydroxycarbonyl, methoxycarbonyl and ethoxycarbonyl; R³ furthermore stands for 5- or 6-membered heterocyclyl having 1 to 3 identical or different hetero atoms, such as nitrogen, oxygen and sulphur atoms, which is optionally fused to 1 or 2 benzene or cyclohexane rings and is optionally monosubstituted, disubstituted or trisubstituted by identical or different substituents, substituents which may be mentioned being: acyl having 2 to 5 carbon atoms, chlorine, bromine, methyl, ethyl, phenyl, oxo and hydroxyl; finally, R³ alternatively stands for alkoxycarbonyl having 1 to 4 carbon atoms in the alkoxy part, or for —OR⁴, —SR⁴ or —NR⁵R⁶;

R⁴ stands for straight-chain or branched alkyl having 1 to 4 carbon atoms which is optionally monosubstituted, disubstituted or trisubstituted by identical or different substituents, suitable substituents being the following: fluorine, chlorine, —OR$^{IV}$, —SR$^{IV}$, —COOR$^I$, —CONR$^{II}$R$^{III}$, CN, NR$^{II}$R$^{III}$, alkylcarbonyl having 1 to 4 carbon atoms in the straight-chain or branched alkyl part, phenyl or phenoxy, each of which is optionally monosubstituted, disubstituted or trisubstituted by identical or different substituents from the series comprising halogen and methyl, cyclopropyl, cyclohexyl, cyclopentenyl or cyclohexenyl, each of which is optionally monosubstituted, disubstituted or trisubstituted by methyl, or 3- to 6-membered heterocyclyl having 1 to 3 identical or different hetero atoms, such as nitrogen, oxygen and sulphur atoms, which is optionally monosubstituted, disubstituted or trisubstituted by identical or different substituents from the series comprising halogen, methyl and ethyl; $R^4$ furthermore stands for allyl or propargyl, each of which is optionally monosubstituted or disubstituted by methyl, or for cyclopropyl, cyclohexyl, cyclopentenyl or cyclohexenyl, each of which is optionally monosubstituted, disubstituted or trisubstituted by methyl;

$R^5$ stands for hydrogen or for straight-chain or branched alkyl having 1 to 4 carbon atoms which is optionally monosubstituted or disubstituted by identical or different substituents, substituents which may preferably be mentioned being: halogen, cyano, —$COOR^I$, —$CONR^{II}R^{III}$, $NR^{II}R^{III}$ —$OR^{IV}$, —$S(O)_nR^{IV}$, acyl having 2 to 9 carbon atoms, phenyl which is optionally monosubstituted, disubstituted or trisubstituted by identical or different substituents from the series comprising halogen and alkyl having 1 to 4 carbon atoms, a 5- or 6-membered heterocyclic ring having 1 to 3 identical or different hetero atoms, in particular nitrogen, oxygen and sulphur, which is optionally monosubstituted, disubstituted or trisubstituted by identical or different substituents from the series comprising halogen and straight-chain or branched alkyl and alkoxy each having 1 to 4 carbon atoms, or cycloalkyl having 3 to 6 carbon atoms or cycloalkenyl having 5 to 7 carbon atoms, each of which is optionally substituted by straight-chain or branched alkyl having 1 to 4 carbon atoms;

$R^5$ furthermore particularly preferably stands for straight-chain or branched alkenyl or alkinyl each having 2 to 6 carbon atoms, for cycloalkenyl having 5 to 7 carbon atoms which is optionally substituted by straight-chain or branched alkyl having 1 to 4 carbon atoms, for optionally substituted cycloalkyl having 3 to 6 carbon atoms, substituents which may preferably be mentioned being: halogen, straight-chain or branched alkyl and alkoxy each having 1 to 4 carbon atoms, cyano, amino, carbamoyl, in each case straight-chain or branched alkylamino, dialkylamino, alkylcarbamoyl and dialkylcarbamoyl each having 1 to 4 carbon atoms in each alkyl part, alkoxycarbonylamino having 1 to 4 carbon atoms in the straight-chain or branched alkoxy part, cycloalkyl and cycloalkylalkyl each having 5 or 6 carbon atoms in the cycloalkyl part and 1 to 4 carbon atoms in the straight-chain or branched alkyl part, or phenyl or pyrrolidone, each of which is optionally monosubstituted, disubstituted or trisubstituted by identical or different substituents from the series comprising halogen and alkyl having 1 to 4 carbon atoms; $R^5$ additionally particularly preferably stands for phenyl which is optionally monosubstituted, disubstituted or trisubstituted by identical or different substituents from the series comprising halogen, straight-chain or branched alkyl or alkoxy each having 1 to 4 carbon atoms, and halogenoalkyl or halogenoalkoxy each having 1 or 2 carbon atoms and 1 to 5 identical or different halogen atoms, or for a 5- or 5-membered heterocyclic ring having 1 to 3 identical or different hetero atoms, such as, in particular, nitrogen, oxygen or sulphur, which is optionally monosubstituted, disubstituted or trisubstituted by identical or different substituents; substituents which may be mentioned for the heterocyclic rings are: halogen, mercapto, phenyl, straight-chain or branched alkyl, alkoxy, alkylthio, alkylsulphinyl and alkylsulphonyl having 1 to 4 carbon atoms per alkyl;

$R^6$ stands for the meanings of $R^5$ or the —$OR^{IV}$ group, or $R^5$ and $R^6$, together with the nitrogen atom to which they are bonded, stand for a monocyclic, bicyclic or tricyclic heterocyclic ring or spiroheterocyclic ring which is optionally monosubstituted to pentasubstituted by identical or different substituents, heterocyclic rings which may be mentioned being: oxazolidine, pyrrolidine, imidazolidine, piperidine, piperazine, morpholine, thiomorpholine, 1,3-oxazane or 1,3-diazane; each of these heterocyclic rings may optionally be fused to 1 or 2 benzene or cyclohexane rings or optionally bridged by methylene or ethylene. Substituents which may be mentioned for all hetero systems are: straight-chain or branched alkyl or cycloalkyl having 3 to 6 carbon atoms, the hydroxyl or the oxo group, straight-chain or branched alkenyl having 2 to b 4 carbon atoms, hydroxycarbonyl, alkoxycarbonyl having 1 to 4 carbon atoms in the straight-chain or branched alkyl part, carbamoyl, alkylcarbamoyl or dialkylcarbamoyl each having 1 to 4 carbon atoms in each alkyl part, and furthermore phenyl or phenylalkyl which has 1 to 4 carbon atoms in the straight-chain or branched alkyl part and each of which is optionally monosubstituted or disubstituted by identical or different substituents from the series comprising halogen and straight-chain or branched alkyl and alkoxy each having 1 to 4 carbon atoms, $R^I$ stands for straight-chain or branched alkyl having 1 to 4 carbon atoms, $R^{II}$ stands for hydrogen, straight-chain or branched alkyl having 1 to 4 carbon atoms, benzyl or phenethyl, each of which is optionally monosubstituted, disubstituted or trisubstituted by identical or different substituents, phenyl substituents which may be mentioned in each case being: fluorine, chlorine, methyl, methoxy and trifluoromethy; $R^{II}$ furthermore stands for alkoxycarbonyl having 1 to 4 carbon atoms in the alkoxy part and 1 or 2 carbon atoms in the alkyl part, carbamoylalkyl having 1 to 2 carbon atoms in the alkyl part, alkylcarbamoylalkyl or dialkylcarbamoylalkyl each having 1 or 2 carbon atoms in each alkyl part, or cycloalkyl having 3 to 6 carbon atoms which is optionally monosubstituted, disubstituted or trisubstituted by identical or different substituents from the series comprising methyl and ethyl, $R^{III}$ stands for the meanings of $R^{II}$, $R^{IV}$ stands for hydrogen, straight-chain or branched alkyl having 1 to 4 carbon atoms, or benzyl or phenethyl, each of which is optionally monosubstituted, disubstituted or trisubstituted by identical or different substituents, phenyl substituents which may be mentioned in each case being: fluorine, chlorine, methyl, methoxy and trifluoromethyl; $R^{IV}$ furthermore stands for acyl having 2 to 9 carbon atoms;

n stands for the numbers 0, 1 or 2, and

X stands for oxygen or sulphur.

Very particularly preferred N,N'-diacylaminals are those of the general formula (I) in which R¹ stands for alkyl having 1 to 2 carbon atoms which is optionally monosubstituted or disubstituted by identical or different substituents, suitable substituents being the following: fluorine, chlorine, cyano, —COOR$^I$, —CONR$^{II}$R$^{III}$, —OR$^{IV}$, alkylcarbonyl having 1 to 4 carbon atoms in the straight-chain or branched alkyl part, phenyl which is optionally monosubstituted, disubstituted or trisubstituted by identical or different substituents from the series comprising fluorine, chlorine and methyl, cyclopropyl or cyclohexyl, each of which is optionally monosubstituted, disubstituted or trisubstituted by methyl, and the following heterocyclic rings:

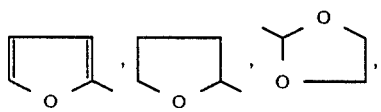

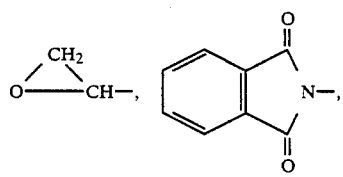

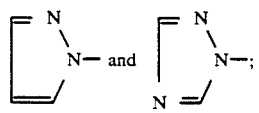

R¹ furthermore stands for allyl or propargyl, or for cyclopropyl, cyclohexyl, cyclopentenyl or cyclohexenyl, each of which is optionally monosubstituted, disubstituted or trisubstituted by methyl;

R² stands for hydrogen or for alkyl having 1 to 4 carbon atoms which is optionally monosubstituted or disubstituted by identical or different substituents, suitable substituents being the following: cyano, methoxy, ethoxy, methylthio, ethylthio, —COOR$^I$, alkylcarbonylamino having 1 to 4 carbon atoms in the straight-chain or branched alkyl part, phenyl which is optionally monosubstituted, disubstituted or trisubstituted by identical or different substituents from the series comprising halogen, methyl and methoxy, cyclopropyl or cyclohexyl, each of which is optionally monosubstituted, disubstituted or trisubstituted by methyl, and the following heterocyclic rings:

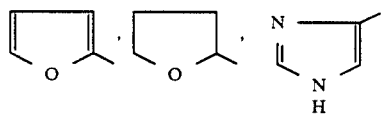

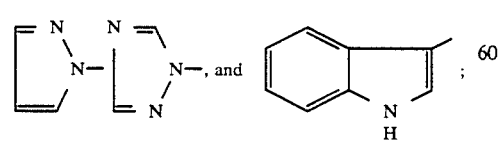

R² furthermore stands for vinyl, allyl, allenyl, ethinyl or propargyl, each of which is optionally substituted by phenyl which may optionally be monosubstituted, disubstituted or trisubstituted by identical or different substituents from the series comprising halogen and methyl; R² in addition stands for cyclopropyl, cyclohexyl, cyclopentenyl or cyclohexenyl; R² additionally stands for phenyl which is optionally monosubstituted, disubstituted or trisubstituted by identical or different substituents from the series comprising halogen, methyl and methoxy, or for the following heterocyclic rings:

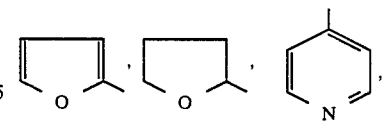

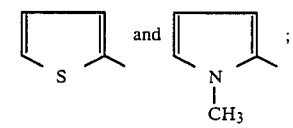

R³ stands for hydrogen or for straight-chain or branched alkyl having 1 to 4 carbon atoms which is optionally monosubstituted or disubstituted by identical or different substituents, suitable substituents being the following: fluorine, chlorine, bromine, iodine, cyano, alkoxy, alkylthio, alkylsulphinyl and alkylsulphonyl each having 1 to 2 carbon atoms, alkylcarbonyloxy having 1 to 4 carbon atoms in the straight-chain or branched alkyl part, formamido, alkylcarbonylamino having 1 or 2 carbon atoms in the alkyl part, which is optionally substituted by fluorine, benzoylamino which is optionally substituted by chlorine, alkoxycarbonylamino having 1 to 4 carbon atoms in the straight-chain or branched alkoxy part, —COOR$^I$, cyclopropyl, cyclopentyl, cyclohexyl or phenyl which is optionally monosubstituted, disubstituted or trisubstituted by identical or different substituents from the series comprising halogen and methyl, and the following heterocyclic rings:

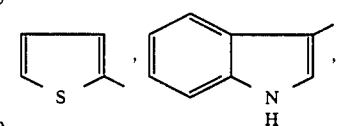

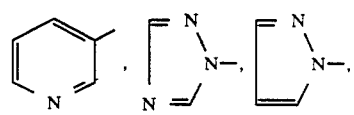

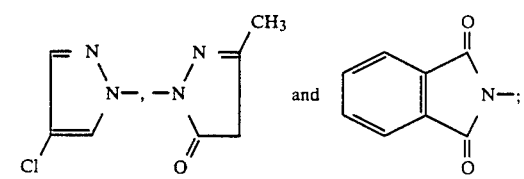

R³ furthermore stands for vinyl or ethinyl, each of which is optionally monosubstituted or disubstituted by identical or different substituents from the series comprising phenyl which may optionally be monosubstituted, disubstituted or trisubstituted by identical or different substituents from the series comprising halogen and methyl, or by methyl; $R^3$ additionally stands for cyclopropyl, cyclopentyl, cyclohexyl, cyclopentenyl or cyclohexenyl, each of which is optionally bridged by methylene or ethylene and/or fused to 1 or 2 benzene, cyclopentane or cyclohexane rings and each of which is optionally monosubstituted, disubstituted or trisubstituted by identical or different substituents, substitutents which may be mentioned being: halogen, methyl, the oxo group, phenyl, hydroxycarbonyl, methoxycarbonyl and ethoxycarbony; the following rings may be mentioned individually:

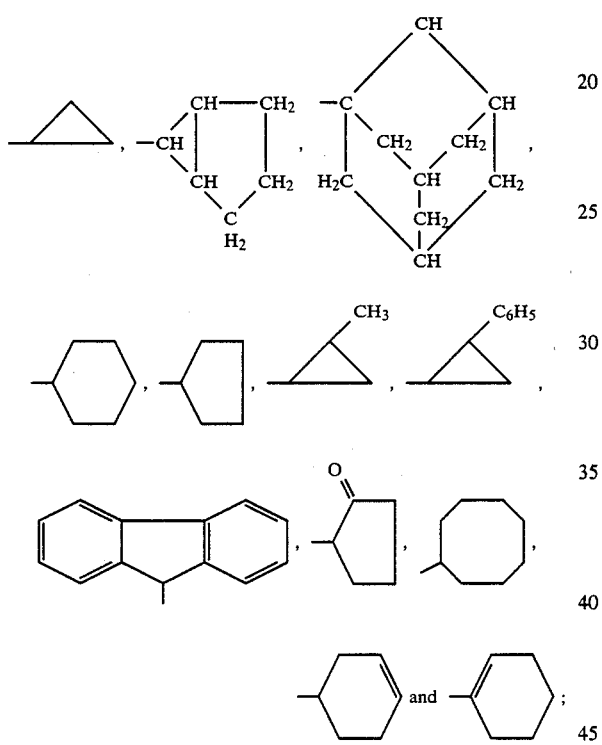

$R^3$ in addition stands for phenyl which is optionally fused to 1 or 2 benzene, cyclopentane or cyclohexane rings and is optionally monosubstituted, disubstituted or trisubstituted by identical or different substituents, substituents which may be mentioned being: fluorine, chlorine, hydroxyl, nitro, methyl, methoxy, acetoxy, acetamido, hydroxycarbonyl, methoxycarbonyl and ethoxycarbonyl; $R^3$ furthermore stands for 5- or 6-membered heterocyclyl having 1 to 3 identical or different hetero atoms, such as nitrogen, oxygen and sulphur atoms, which is optionally fused to 1 or 2 benzene or cyclohexane rings and is optionally monosubstituted, disubstituted or trisubstituted by identical or different substituents, substituents which may be mentioned being: acyl having 2 to 5 carbon atoms, chlorine, bromine, methyl, ethyl, phenyl, the oxo group and hydroxyl; the following heterocyclic rings may be mentioned individually:

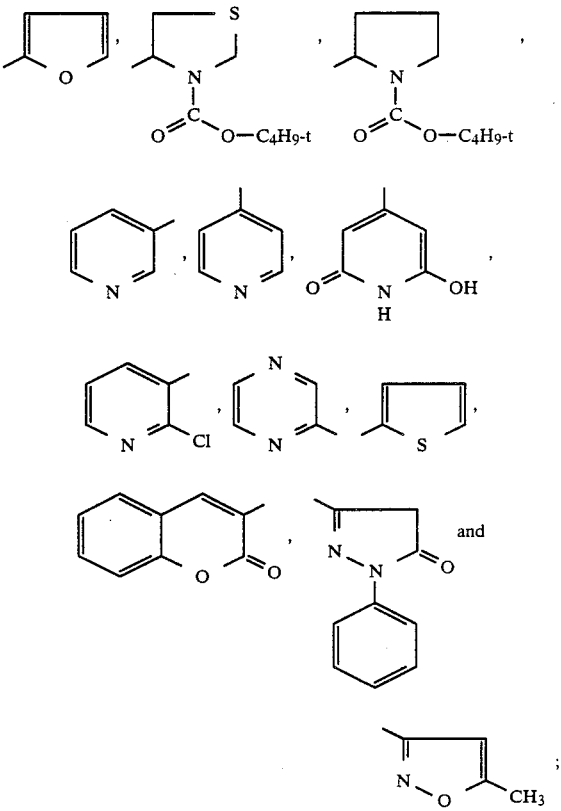

Finally, $R^3$ alternatively stands for alkoxycarbonyl having 1 to 4 carbon atoms in the straight-chain or branched alkoxy part, or for $-OR^4$, $-SR^4$ or $-NR^5R^6$;

$R^4$ stands for straight-chain or branched alkyl having 1 or 2 carbon atoms which is optionally monosubstituted or disubstituted by identical or different substituents, suitable substituents being the following: fluorine, chlorine, methoxy, ethoxy, methylthio, alkoxycarbonyl having 1 to 4 carbon atoms in the straight-chain or branched alkyl part, carbamoyl, methylcarbamoyl, dimethylcarbamoyl, cyano, dimethylamino, diethylamino, acetyl, pivaloyl, or phenyl or phenoxy, each of which is optionally monosubstituted, disubstituted or trisubstituted by identical or different substituents from the series comprising halogen and methyl, and cyclopropyl or cyclohexyl, each of which is optionally monosubstituted, disubstituted or trisubstituted by methyl; $R^4$ furthermore stands for 3- to 6-membered heterocyclyl having 1 to 3 identical or different hetero atoms, such as nitrogen, oxygen and sulphur atoms, which is optionally monosubstituted, disubstituted or trisubstituted by identical or different substituents from the series comprising halogen, methyl and ethyl; the following heterocyclic rings may be mentioned individually:

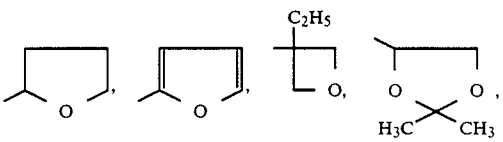

-continued

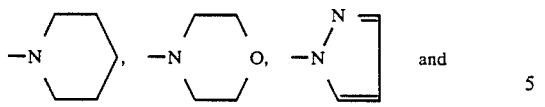 and

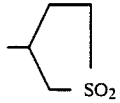

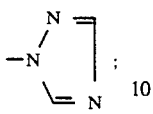

R⁴ in addition stands for allyl or propargyl, each of which is optionally monosubstituted or disubstituted by methyl, or for cyclohexyl which is optionally monosubstituted, disubstituted or trisubstituted by methyl;

R⁵ stands for hydrogen, straight-chain or branched alkyl having 1 to 4 carbon atoms, or alkyl having 1 to 3 carbon atoms which is monosubstituted or disubstituted by identical or different substituents, suitable substituents being: chlorine, hydroxyl, alkylcarbonyloxy having 1 to 4 carbon atoms in the straight-chain or branched alkyl part, alkylcarbonyl having 1 to 4 carbon atoms in the straight-chain or branched alkyl part, alkoxy and alkylthio each having 1 or 2 carbon atoms, alkoxycarbonyl having 1 to 4 carbon atoms in the straight-chain or branched alkoxy part, carbamoyl, methylcarbamoyl, dimethylcarbamoyl, cyano, dimethylamino, diethylamino, 2-furyl, 2-pyridyl, 1-morpholino, cyclopropyl, cyclohexyl or phenyl which is optionally monosubstituted, disubstituted or trisubstituted by identical or different substituents from the series comprising chlorine and methyl; R⁵ furthermore very particularly preferably stands for allyl or propargyl, for 1-cyclohexenyl, or for cyclohexyl which is monosubstituted, disubstituted or trisubstituted by identical or different substituents, suitable substituents being: chlorine, methyl, ethyl, methoxy, cyano, amino, alkylamino and dialkylamino each having 1 or 2 carbon atoms in each alkyl part, carbamoyl, alkylcarbamoyl and dialkylcarbamoyl each having 1 or 2 carbon atoms in each alkyl part, cyclohexyl, cyclohexylalkyl having 1 or 2 carbon atoms in the alkyl part, or 1-pyrrolidin-2-one; R⁵ in addition very particularly preferably stands for phenyl which is optionally monosubstituted, disubstituted or trisubstituted by identical or different substituents from the series comprising chlorine and methyl, for 2-pyridyl or 2-pyrimidinyl, each of which is optionally monosubstituted, disubstituted or trisubstituted by methyl, for 2-thiazolyl which is optionally substituted by phenyl, for 2-benzothiazolyl which is optionally monosubstituted, disubstituted or trisubstituted by identical or different substituents from the series comprising chlorine, methyl and methoxy, for 1,2,4-triazol-3-yl, for 1,2,4-thiadiazol-5-yl which is optionally substituted by phenyl, for 1,3,4-thiadiazol-5-yl which is optionally monosubstituted, disubstituted or trisubstituted by identical or different substituents from the series comprising mercapto, straight-chain or branched alkyl having 1 to 4 carbon atoms, and in each case straight-chain or branched alkylthio, alkylsulphinyl and alkylsulphonyl each having 1 to 4 carbon atoms, or for the

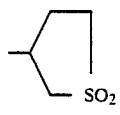

group,

R⁶ stands for hydrogen, straight-chain or branched alkyl having 1 to 4 carbon atoms, or alkyl having 1 to 3 carbon atoms which is monosubstituted or disubstituted by identical or different substituents, substituents which may be mentioned being: chlorine, hydroxyl, alkylcarbonyloxy having 1 to 4 carbon atoms in the straight-chain or branched alkyl part, alkylcarbonyl having 1 to 4 carbon atoms in the straight-chain or branched alkyl part, alkoxy and alkylthio each having 1 or 2 carbon atoms, alkoxycarbonyl having 1 to 4 carbon atoms in the straight-chain or branched alkoxy part, carbamoyl, methylcarbamoyl, dimethylcarbamoyl, cyano, dimethylamino, diethylamino, or 2-furyl, 2-pyridyl, 1-morpholino, cyclopropyl, cyclohexyl or phenyl which is optionally monosubstituted, disubstituted or trisubstituted by identical or different substituents from the series comprising chlorine and methyl; R⁶ furthermore very particularly preferably stands for allyl or propargyl, for 1-cyclohexenyl, or for cyclohexyl which is monosubstituted, disubstituted or trisubstituted by identical or different substituents, substituents which may be mentioned being: chlorine, methyl, ethyl, methoxy, cyano, amino, alkylamino or dialkylamino each having 1 or 2 carbon atoms in each alkyl part, carbamoyl, alkylcarbamoyl or dialkylcarbamoyl each having 1 or 2 carbon atoms in each alkyl part, cyclohexyl, cyclohexylalkyl having 1 or 2 carbon atoms in the alkyl part, or 1-pyrrolidin-2-one; R⁶ in addition very particularly preferably stands for phenyl which is optionally monosubstituted, disubstituted or trisubstituted by identical or different substituents from the series comprising chlorine and methyl, for 2-pyridyl or 2-pyrimidyl, each of which is optionally monosubstituted, disubstituted or trisubstituted by methyl, for 2-thiazolyl which is optionally substituted by phenyl, for 2-benzothiazolyl which is optionally monosubstituted, disubstituted or trisubstituted by identical or different substituents from the series comprising chlorine, methyl and methoxy, for 1,2,4-triazol-3-yl, for 1,2,4-thiadiazol-5-yl which is optionally substituted by phenyl, for 1,3,4-thiadiazol-5-yl which is optionally monosubstituted, disubstituted or trisubstituted by identical or different substituents from the series comprising mercapto, straight-chain or branched alkyl having 1 to 4 carbon atoms, and in each case straight-chain or branched alkylthio, alkylsulphinyl and alkylsulphonyl each having 1 to 4 carbon atoms, or for the

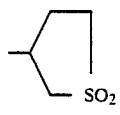

group, R⁶ additionally very particularly preferably stands for hydroxyl, alkoxy having 1 or 2 carbon atoms, for benzyloxy which is optionally monosubstituted, disubstituted or trisubstituted by identical or different substituents from the series comprising chlorine and methyl, for 1-adamantyl, 2-norbornyl, 1- or 2-decalyl or 1- or 2-tertralyl; or $R^5$ and $R^6$, together with the nitrogen atom to which they are bonded, stand for the following monocyclic, bicyclic or tricyclic heterocyclic rings or spiroheterocyclic rings:

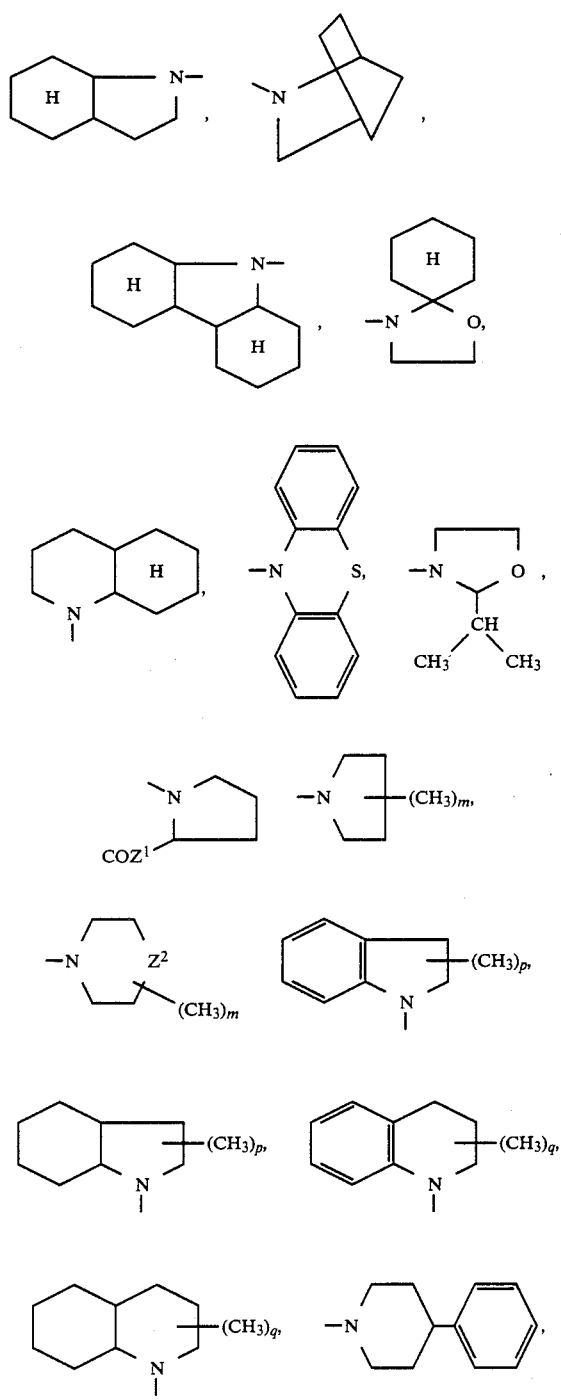

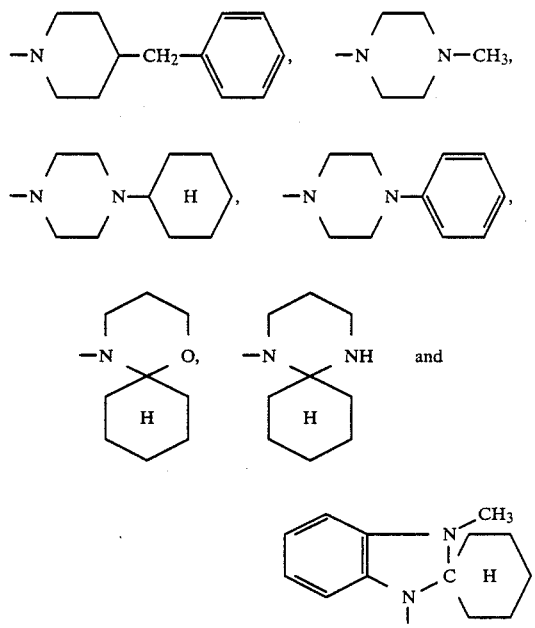

where $Z^1$ stands for hydroxyl, methoxy, ethoxy, amino, methylamino, ethylamino, dimethylamino or methylethylamino, $Z^2$ stands for oxygen or the $CH_2$ group, m stands for the numbers 0, 1, 2, 3 or 4, p stands for the numbers 0, 1 or 2, q stands for the numbers 0, 1, 2 or 3, $R^I$ stands for methyl, ethyl, n- or i-propyl and n-, i-, s- or t-butyl, $R^{II}$ and $R^{III}$ are identical or different and stand for hydrogen, methyl, ethyl, n- or i-propyl, for benzyl which is optionally monosubstituted, disubstituted or trisubstituted by identical or different substituents, with chlorine and methyl as substituents, for alkoxycarbonylalkyl having 1 or 2 carbon atoms in each alkyl part, for carbamoylalkyl, alkylcarbamoylalkyl or dialkylcarbamoylalkyl each having 1 or 2 carbon atoms in each alkyl part, or for cyclohexyl which is optionally monosubstituted, disubstituted or trisubstituted by methyl, $R^{IV}$ stands for hydrogen, alkyl having 1 or 2 carbon atoms, for benzyl which is optionally monosubstituted, disubstituted or trisubstituted by identical or different substituents, phenyl substituents which may be mentioned being fluorine, chlorine and methyl; and X stands for oxygen or sulphur.

Apart from the compounds mentioned in the preparation examples, the substances of the formula (I) listed in the table below may be mentioned as examples of compounds according to the invention:

$$R^1-O-N=C\begin{smallmatrix}CN\\|\\CO-NH-CH-NH-CX-R^3\\|\\R^2\end{smallmatrix}$$ (I)

| R¹ | R² | R³ | X |
|---|---|---|---|
| CH₃ | H | H | O |
| CH₃ | H | —CH₂—O—CH₃ | O |
| CH₃ | H | —CHCl₂ | O |
| CH₃ | H | —CH₂—C₆H₅ | O |
| CH₃ | H | cyclopropyl | O |
| CH₃ | H | —C₆H₄—Cl (p) | O |
| CH₃ | H | —C₆H₄—OCH₃ (p) | O |
| CH₃ | H | —C₆H₄—CH₃ (p) | O |
| CH₃ | H | —C₆H₃(Cl)₂ (3,4) | O |
| CH₃ | H | —CH₂—N(1,2,4-triazolyl) | O |
| CH₃ | H | 2-methylfuryl | O |
| CH₃ | H | —O—CH(CH₃)₂ | O |
| CH₃ | H | —O—CH₂—C₆H₅ | O |
| CH₃ | H | —O—C₆H₅ | O |
| CH₃ | H | —N(C₂H₅)₂ | O |
| CH₃ | H | —NH—cyclohexyl | O |

-continued $$R^1-O\sim N=C\begin{matrix}CN\\CO-NH-CH-NH-CX-R^3\\|\\R^2\end{matrix} \quad (I)$$

| $R^1$ | $R^2$ | $R^3$ | X |
|---|---|---|---|
| CH₃ | H | —S—C₂H₅ | O |
| CH₃ | H | —NH—CH₃ | S |
| CH₃ | H | —NH—C₆H₅ | O |
| CH₃ | CH₃ | CH₃ | O |
| CH₃ | —CH₂—C₆H₅ | CH₃ | O |
| —CH₂—C≡N | H | CH₃ | O |
| —CH₂—C₆H₅ | H | CH₃ | O |
| CH₃ | H | —CO—OC₂H₅ | O |
| CH₃ | H | —O—CH₂—CCl₃ | O |
| CH₃ | H | —O—CH₂CH₂—OCH₃ | O |
| CH₃ | H | —O—CH(CH₃)—CO—OC₂H₅ | O |
| CH₃ | H | —O—CH₂CH₂—CN | O |
| CH₃ | H | —O—CH₂—CO—NH₂ | O |
| CH₃ | H | —O—CH₂CH₂—N(CH₃)₂ | O |
| CH₃ | H | —O—CH₂CH₂—N(morpholino) | O |
| CH₃ | H | —O—CH₂—N(1,2,4-triazolyl) | O |
| CH₃ | H | —O—CH₂—(2-furyl) | O |
| CH₃ | H | —O—CH₂—cyclopropyl | O |
| CH₃ | H | —O—CH₂—CH₂—O—C₆H₅ | O |
| CH₃ | H | —O—CH₂—CH=CH₂ | O |
| CH₃ | H | —O—CH₂—C≡CH | O |
| CH₃ | H | —O—cyclohexyl | O |

-continued $$R^1-O-N=C\begin{smallmatrix}CN\\|\\CO-NH-CH-NH-CX-R^3\\|\\R^2\end{smallmatrix}$$ (I)

| $R^1$ | $R^2$ | $R^3$ | X |
|---|---|---|---|
| CH$_3$ | H | —CH$_2$—S—CH$_3$ | O |
| CH$_3$ | H | —CH$_2$—SO$_2$—CH$_3$ | O |
| CH$_3$ | H | —CH=CH$_2$ | O |
| CH$_3$ | H | —CH$_2$—C≡N | O |
| CH$_3$ | H | —CH$_2$—O—CO—CH$_3$ | O |
| CH$_3$ | H | —CH$_2$—NH—CO—CH$_3$ | O |
| CH$_3$ | H | —CH$_2$—CO—OCH$_3$ | O |
| CH$_3$ | H | —CH$_2$—(2-thienyl) | O |
| CH$_3$ | H | —(cyclohexenyl) | O |
| CH$_3$ | H | —CH$_2$—CH$_2$—(cyclohexyl) | O |
| CH$_3$ | H | —(adamantyl) | O |
| CH$_3$ | H | —(2-hydroxyphenyl) | O |
| CH$_3$ | H | —(3-pyridyl) | O |
| CH$_3$ | H | —(3-methyl-5-methylisoxazolyl) | O |
| CH$_3$ | H | —(2-pyrrolidinyl-N-CO-O-C$_4$H$_9$-t) | O |
| CH$_3$ | H | —NH$_2$ | O |
| CH$_3$ | H | —N(morpholino) | O |

-continued

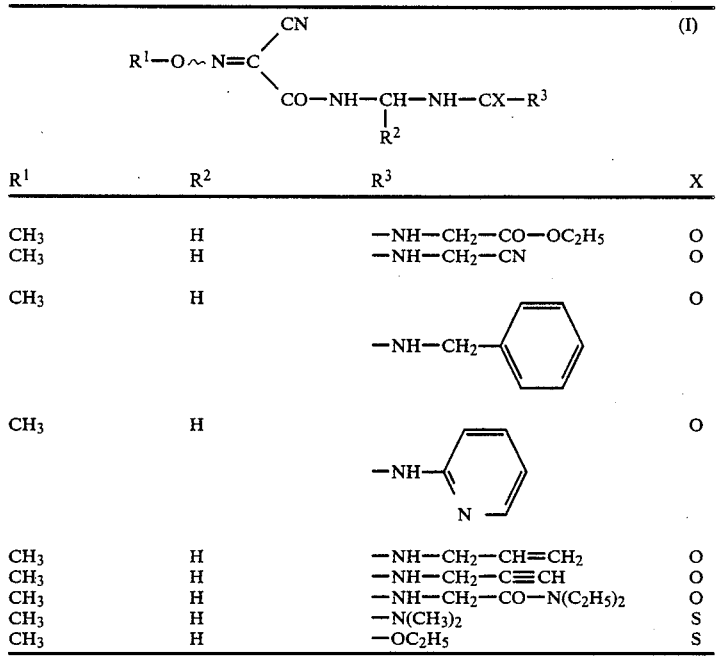

| R¹ | R² | R³ | X |
|---|---|---|---|
| CH₃ | H | —NH—CH₂—CO—OC₂H₅ | O |
| CH₃ | H | —NH—CH₂—CN | O |
| CH₃ | H | —NH—CH₂—C₆H₅ | O |
| CH₃ | H | —NH—(2-pyridyl) | O |
| CH₃ | H | —NH—CH₂—CH=CH₂ | O |
| CH₃ | H | —NH—CH₂—C≡CH | O |
| CH₃ | H | —NH—CH₂—CO—N(C₂H₅)₂ | O |
| CH₃ | H | —N(CH₃)₂ | S |
| CH₃ | H | —OC₂H₅ | S |

If, for example, N-aminomethyl-(E)-2-cyano-2-methoximinoacetamide hydrochloride is used as starting material, acetyl chloride as acylating reagent and triethylamine as base and 4-dimethylaminopyridine as catalyst, the course of process (a) according to the invention may be represented by the following equation:

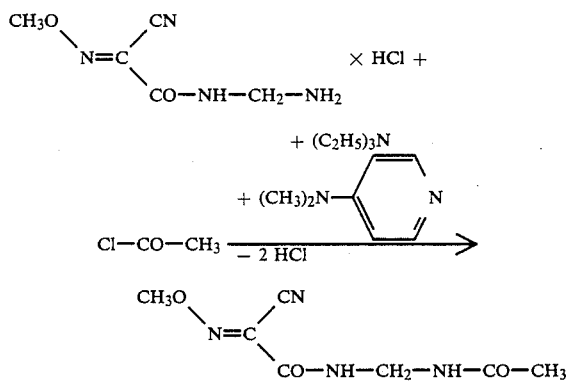

If, for example, (E)-2-cyano-2-methoximinoacetaminomethyl isocyanate and methylamine are used as starting materials, the course of the process (b) according to the invention may be represented by the following equation:

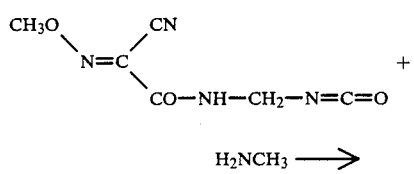

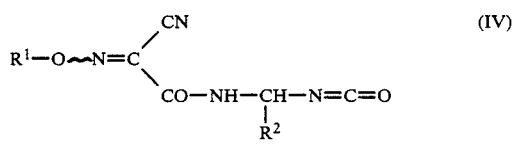

Formula (II) provides a general definition of the 2-cyano-2-oximino-acetamides to be used as starting materials for carrying out process (a) according to the invention. In this formula, R¹ and R² have the meanings which have already been mentioned for these substituents in connection with the description of the substances of formula (I) according to the invention, including the preferred, particularly preferred and very particularly preferred meanings hereinabove. HY preferably stands for the equivalent of a mineral acid, such as, for example, hydrochloric acid, or of a carboxylic acid, such as, for example, oxalic acid.

The 2-cyano-2-oximino-acetamides of the formula (II) were hitherto unknown. However, they can be prepared in a known fashion by hydrolyzing isocyanates of the formula (IV)

$$R^1-O-N=C\begin{matrix}CN\\CO-NH-CH-N=C=O\\|\\R^2\end{matrix} \quad (IV)$$

in which

R¹ and R² have the abovementioned meaning,
in a customary fashion, and isolating the resultant amine as a salt in a customary fashion.

The hydrolysis of the isocyanates of the formula (IV) is carried out in the presence of a diluent. The following are preferably suitable in this case: water; nitriles, such as acetonitrile; ethers, such as tetrahydrofuran, dioxane or dimethyl ether, or ketones, such as acetone.

The reaction temperatures may be varied within a relatively wide range in the hydrolysis of the isocyanates of the formula (IV). In general, the hydrolysis is carried out at between −20° C. and 150° C., preferably between 20° C. and 80° C.

When carrying out the hydrolysis of the isocyanates of the formula (IV), the latter are preferably reacted in situ (for the preparation, see the description of process (b) according to the invention) with excess water. The resultant amine is isolated as a salt by adding the acid, for example hydrochloric acid, and subsequently carrying out the customary work-up.

Formulae (IIIa) and (IIIb) provide general definitions of the acylating reagents additionally to be used as starting materials for carrying out process (a) according to the invention. In the formula (IIIa), X preferably stands for oxygen or sulphur and Z preferably stands for a leaving group. These preferably include chlorine, bromine, alkoxy and alkylthio each having 1 to 4 carbon atoms, carboxymethoxy, carboxymethylthio and the $-O-CO-R^3$, $-O-CO-OR^4$ and $SR^4$ groups. $R^3$ and $R^4$ here preferably have the meanings which have already preferably been mentioned for these substituents in connection with the description of the substances of the formula (I) according to the invention. In the formula (IIIb), X and $R^6$ preferably have the meanings which have already preferably been mentioned for these substituents in connection with the description of the substances of the formula (I) according to the invention.

The acylating reagents of the formulae (IIIa) and (IIIb), i.e. carbonyl halides, carboxylic anhydrides, halogenoformates and halogenothioformates, trithiocarbonates, pyrocarbonates, carbamoyl halides, carbamates, thiocarbamates, dithiocarbamates, isocyanates or isothiocyanates, are generally known compounds of organic chemistry or can be obtained by generally customary methods.

Formula (IV) provides a general definition of the isocyanates to be used as starting materials for carrying out process (b) according to the invention and as precursors for process (a) according to the invention. In this formula, $R^1$ and $R^2$ have the meanings which have already been mentioned for these substituents in connection with the description of the substances of the formula (I) according to the invention, including the preferred, particularly preferred and very particularly preferred meanings hereinabove.

The isocyanates of the formula (IV) were hitherto unknown. However, they can be prepared in a known fashion, for example by (α) oxidizing amides of the general formula (VI)

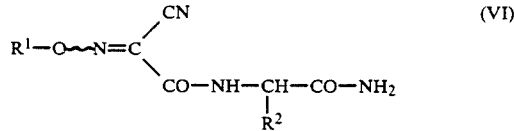

in which
$R^1$ and $R^2$ have the abovementioned meaning, in a customary fashion, if appropriate in the presence of a diluent ("Hofmann degradation"), it being possible to further react the resultant isocyanates of the formula (IV) directly, if desired also without isolation; or (β) warming azides of the general formula (VII)

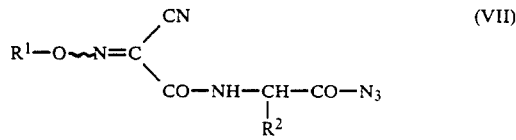

in which
$R^1$ and $R^2$ have the abovementioned meaning, in the presence of a diluent ("Curtius degradation"), it being possible to further react the resultant isocyanates of the formula (IV) directly, if desired also without isolation.

Oxidants which may preferably be mentioned for process variant (α) are: sodium hypochlorite, sodium hypobromite, lead tetraacetate and I,I-bis(trifluoroacetoxy)-iodobenzene [

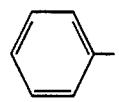

I(OCOCF$_3$)$_2$ = J. Chem. Soc. Chem. Com. 1982, p. 280].

Suitable diluents for process variant (α) are inert organic solvents, such as, for example, ethers, such as tetrahydrofuran, dioxane or dimethyl ether, or nitriles, such as acetonitrile. In the case of direct further reaction of the isocyanates of the formula (IV), suitable diluents are also water or alcohols, or mixtures thereof with inert organic solvents, such as, for example, water-/acetonitrile.

The reaction temperatures may be varied within a relatively wide range in the oxidation in accordance with process variant (α). In general, the oxidation is carried out between −20° C. and 120° C., preferably between 0° C. and 40° C.

When carrying out the oxidation in accordance with process variant (α), a slight excess of oxidant is preferably used, the isocyanates of the formula (IV) generally being further reacted directly without isolation.

Suitable diluents for process variant (β) are inert organic solvents, such as, for example, aromatic hydrocarbons, such as toluene or chlorobenzene; ethers, such as dioxane, or halogenated hydrocarbons, such as chloroform or methylene chloride. In the case of direct further reaction of the isocyanates of the formula (IV), suitable diluents are also water or alcohols, or mixtures thereof with inert organic solvents.

The reaction temperatures may be varied within a relatively wide range when carrying out process variant (β). In general, the process is carried out between 0° C. and 150° C., preferably between 60° C. and 100° C.

When carrying out process variant (β), the resultant isocyanates of the formula (IV) are generally further reacted directly without isolation.

The amides of the formula (VI) and the azides of the formula (VII) are known (in this respect, compare, for example, EP-OS (European Published Specification) 0,206,004 and DE-OS (German Published Specification) 3,602,243), or can be obtained by the processes described therein.

Formulae (Va) and (Vb) provide general definitions of the protic nucleophiles additionally to be used as starting materials for carrying out process (b) according to the invention. In the formula (Va), $R^3$ preferably stands for the meanings which have already preferably been mentioned for these substituents in connection with the description of the substances of the formula (I) according to the invention. In the formula (Vb), $R^7$ preferably stands for the $-OR^4$, $-SR^4$ or $-NR^5R^6$ groups. $R^4$, $R^5$ and $R^6$ here preferably have the meanings which have already preferably been mentioned for these substituents in connection with the description of the substances of the formula (I) according to the invention.

The protic nucleophiles of the formulae (Va) and (Vb), i.e. carboxylic acids, alcohols, thiols and amines, are generally known compounds of organic chemistry or can be obtained by generally customary methods.

Suitable diluents for process (a) according to the invention are inert organic solvents. These preferably include aromatic hydrocarbons, such as toluene; halogenated hydrocarbons, such as methylene chloride or chloroform; ethers, such as tetrahydrofuran or 1,2-dimethoxyethane; esters, such as ethyl acetate; nitriles, such as acetonitrile; ketones, such as acetone; tertiary amines, such as pyridine; amines, such as dimethylformamide, or alternatively an appropriate excess of the acylating reagent of the formulae (IIIa) and (IIIb).

Process (a) is carried out in the presence of a base. In this case, suitable bases are customary organic and inorganic bases. Tertiary amines, such as triethylamine or pyridine; alkoxides, such as sodium methoxide, and alkali metal carbonates, such as potassium carbonate, may be mentioned preferentially.

Process (a) according to the invention is carried out, if necessary, in the presence of a catalyst. Examples mentioned are the tertiary amines, such as 4-dimethylaminopyridine, 1,8-diazabicyclo[5,4,0]undec-7-ene (DBU) or 1,4-diazabicyclo[2,2,2]-octane (DABCO); furthermore imidazole and dimethylformamide.

The reaction temperatures may be varied within a relatively wide range when carrying out process (a) according to the invention. In general, the process is carried out between $-20°$ C. and $120°$ C., preferably between $0°$ C. and $40°$ C.

When carrying out process (a) according to the invention, equimolar amounts are preferably used, but it is also possible to employ the 2-cyano-2-oximinoacetamides of the formula (II) of the acylating reagents of the formula (IIIa) and (IIIb) in excess. The reaction is carried out, and the reaction products of the formula (I) are worked up and isolated in a generally customary fashion.

Suitable diluents for process (b) according to the invention are inert organic solvents. These preferably include aromatic hydrocarbons, such as toluene; halogenated hydrocarbons, such as methylene chloride; ethers, such as tetrahydrofuran or dimethoxyethane; esters, such as ethyl acetate; nitriles, such as acetonitrile, or alternatively an appropriate excess of a protic nucleophile of the formulae (Va) and (Vb).

Process (b) according to the invention is carried out, if necessary, in the presence of a catalyst. Examples which may be mentioned are the catalysts mentioned above in the case of process (a).

The reaction temperatures may be varied within a relatively wide range when carrying out process (b) according to the invention. In general, the process is carried out between $-20°$ C. and $150°$ C., preferably between $20°$ C. and $80°$ C.

When carrying out process (b) according to the invention, the isocyanate of the formula (IV) is preferably reacted in situ with an excess of a nucleophile of the formulae (Va) or (Vb), the latter simultaneously being used as a solvent. However, it is also possible to react the isolated isocyanates of the formula (IV) in equimolar amounts with the nucleophiles of the formulae (Va) and (Vb). The reaction is carried out and the reaction products of the formula (I) are worked up and isolated in a generally customary fashion.

The active compounds according to the invention have a strong microbicidal action and can be employed in practice for combating undesired microorganisms. The active compounds are suitable for use as pesticides.

For example fungicidal agents in plant protection are employed for combating Plasmodiophoromycetes, Oomycetes, Chytridiomycetes, Zygomycetes, Ascomycetes, Basidiomycetes and Deuteromycetes.

Some causative organisms of fungal and bacterial diseases which come under the generic names listed above may be mentioned as examples, but not by way of limitation: Pythium species, such as, for example, *Pythium ultimum;* Phytophthora species, such as, for example, *Phytophthora infestans;* Pseudoperonospora species, such as, for example, *Pseudoperonospora humuli* or *Pseudoperonospora cubensis;* Plasmopara species, such as, for example, *Plasmopara viticola;* Peronospora species, such as, for example, *Peronospora pisi* or *P. brassicae;* Erysiphe species, such as, for example, *Erysiphe graminis;* Sphaerotheca species, such as, for example, *Sphaerotheca fuliginea;* Podosphaera species, such as, for example, *Podosphaera leucotricha;* Venturia species, such as, for example, *Venturia inaequalis;* Pyrenophora species, such as, for example, *Pyrenophora teres* or *P. graminea* (conidia form: Drechslera, syn: Helminthosporium); Cochliobolus species, such as, for example, *Cochliobolus sativus* (conidia form: Drechslera, syn: Helminthosporium); Uromyces species, such as, for example, *Uromyces appendiculatus;* Puccinia species, such as, for example, *Puccinia recondita;* Tilletia species, such as, for example, *Tilletia caries;* Ustilago species, such as, for example, *Ustilago nuda* or *Ustilago avenae;* Pellicularia species, such as, for example, *Pellicularia sasakii;* Pyricularia species, such as, for example, *Pyricularia oryzae;* Fusarium species, such as, for example, *Fusarium culmorum;* Botrytis species, such as, for example, *Botrytis cinerea;* Septoria species, such as, for example, *Septoria nodorum;* Leptosphaeria species, such as, for example, *Leptosphaeria nodorum;* Cercospora species, such as, for example, *Cercospora canescens* and Pseudocercosporella species, such as, for example, *Pseudocercosporella herpotrichoides.*

The good toleration, by plants, of the active compounds, at the concentrations required for combating plant diseases, permits treatment of above-ground parts of plants, of vegetative propagation stock and seeds, and of the soil.

In pesticides, the active compounds according to the invention can be employed particularly successfully for combating Phytophthora species, such as, for example, *Phytophthora infestans,* in tomatoes; and also for combating Plasmopara species, such as, for example, *Plasmopara viticola,* in vines.

The active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, as well as ULV cold mist and warm mist formulations.

These formulations are produced in known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulfoxide, as well as water; by liquefied gaseous extenders or carriers are meant liquids which are gaseous at normal temperature and under normal pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly disperse silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95% by weight of active compound, preferably between 0.5 and 90%.

The active compounds according to the invention can be present in the formulations or in the various use forms as a mixture with other known active compounds, such as fungicides, bactericides, insecticides, acaricides, nematicides, herbicides, bird repellents, growth factors, plant nutrients and agents for improving soil structure.

The active compounds can be used as such or in the form of their formulations or the use forms prepared therefrom by further dilution, such as ready-to-use solutions, emulsions, suspensions, powders, pastes and granules. They are used in the customary manner, for example by watering, immersion, spraying, atomizing, misting, vaporizing, injecting, forming a slurry, brushing on, dusting, scattering, dry dressing, moist dressing, wet dressing, slurry dressing or encrusting.

In the treatment of parts of plants, the active compound concentrations in the use forms can be varied within a relatively wide range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02% by weight, are required at the place of action.

Preparation examples

EXAMPLE 1

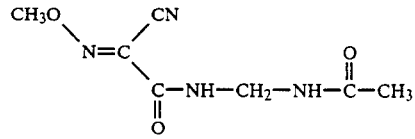

(Process a)

7.7 g (0.04 mol) of N-aminomethyl-(E)-2-cyano-2-methoximino-acetamide hydrochloride are suspended in 150 ml of methylene chloride, and 3.2 g (0.04 mol) of acetyl chloride and subsequently a solution of 8.08 g of triethylamine and 0.49 g (0.004 mol) of 4-dimethylaminopyridine in 40 ml of methylene chloride are added dropwise at 0° C. The mixture is stirred for 1 hour at 0° C. and for 18 hours at room temperature, washed twice each with 1 molar citric acid, 10 percent strength sodium bicarbonate solution and saturated sodium chloride solution, dried over sodium sulphate and evaporated in vacuo.

3.7 g are obtained as the first crude fraction.

The combined washings are extracted by shaking 5 times with methylene chloride, and the combined extracts are dried over sodium sulphate and evaporated. The residue (2.8 g) is recrystallized from isopropanol/petroleum ether together with the 1st fraction. 4.96 g (62% of theory) of N-acetamidomethyl-(E)-2-cyano-2-methoximinoacetamide of melting point 162°–163° C. are obtained.

Preparation of the starting material

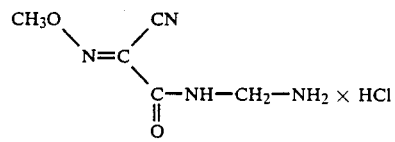

31 g (0.07 mol) of I,I-bis-(trifluoroacetoxy)iodobenzene (98% purity) are added to a solution of 12.4 g (0.067 mol) of N$^\alpha$-[(E)-2-cyano-2-methoximinoacetyl]-glycinamide in 150 ml of acetonitrile/water (1:1), and the mixture is stirred at room temperature for 5 hours while nitrogen is passed through. The mixture is evaporated in vacuo, the oily residue is dried by evaporating twice with ethyl acetate and dissolved in 70 ml of ethyl acetate, and 10 ml of a 25 percent strength ethereal hydrogen chloride solution are added. The precipitate is triturated in a mortar with ether and recrystallized from acetonitrile/ether.

9.8 g (76% of theory) of N-aminomethyl-(E)-2-cyano-2-methoximinoacetamide hydrochloride of melting point 122°–124° C. (decomposition) are obtained.

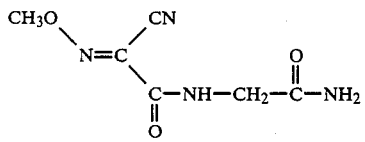

Ammonia is passed into a solution of 56.6 g (0.252 mol) of N-[(E)-2-cyano-2-methoximinoacetyl]-glycine ethyl ester (95 percent purity) in 300 ml of isopropanol at 0° to 10° C. until saturation is achieved, and the mixture is left to stand at room temperature for 4 days. During this time, ammonia is passed in a further twice. After cooling to 0° C., the precipitate is filtered off under suction, washed with cold isopropanol and dried at room temperature.

32 g (69% of theory) of $N^\alpha$-[(E)-2-cyano-2-methoximinoacetyl]-glycinamide of melting point 170°–172° C. are obtained.

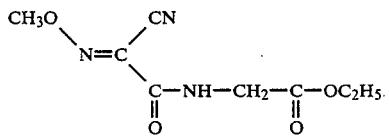

60.5 g (0.427 mol) of glycine ethyl ester hydrochloride are suspended in 450 ml of dichloromethane, 86.2 g (0.853 mol) of triethylamine and 5.2 g (0.043 mol) of 4-dimethylaminopyridine are added, the reaction mixture is stirred at 20° C. for 15 minutes, and a solution of 62.5 g (0.427 mol) of 2-cyano-2-methyl-oximino-acetyl chloride (E isomer) is added dropwise at 0° C. over one hour. The reaction mixture is subsequently stirred for one hour at 0° C. and then for 5 hours at room temperature, and the solution is allowed to stand at room temperature for 2 days. After washing with 1M hydrochloric acid (twice with 300 ml in each case), saturated sodium bicarbonate solution (twice with 200 ml in each case) and water (twice with 300 ml in each case), the solution is dried over sodium sulphate and evaporated in vacuo.

81.0 g (89% of theory) of N-(2-cyano-2-methoximino-acetyl)-glycine ethyl ester (E isomer) are obtained as a brown oil of refractive index $n_D^{23} = 1.4699$.

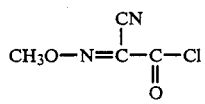

20 g (0.12 mol) of the potassium salt of 2-cyano-2-methoximinoacetate (E isomer) are suspended in 250 ml of dry ether, and 76.2 g (0.6 mol) of oxalyl chloride are added dropwise at 0° C. after addition of a few drops of dimethylformamide. The reaction mixture is stirred at 0° C. for 2 hours and filtered, and the filtrate is evaporated in vacuo at room temperature.

13.7 g (77% of theory) of 2-cyano-2-methoximinoacetyl chloride (E isomer) are obtained as a yellow oil, which is immediately reacted further.

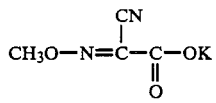

A solution of 45.1 g (0.806 mol) of potassium hydroxide in 500 ml of water is added dropwise to a solution of 124.8 g (0.672 mol) of 84% purity ethyl 2-cyano-2-methoximinoacetate (E isomer) in 500 ml of ethanol at 20° C., and the reaction mixture is stirred at 40° C. for one hour. The solution is evaporated in vacuo at 40° C., and the residue is stirred for 30 minutes with methanol, filtered off under suction, washed with ethanol, acetonitrile and dichloromethane and dried at room temperature.

58.6 g (53% of theory) of the potassium salt of 2-cyano-2-methoximino-acetate (E isomer) are obtained.

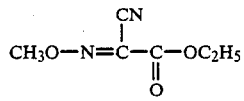

161 g (1.25 mols) of dimethyl sulphate (98% purity) are added dropwise over 30 minutes to a suspension of 164 g (1 mol) of ethyl 2-cyano-2-hydroximinoacetate, sodium chloride (G. Kinast, Liebigs Ann. Chem., 1981, 1561) and 138 g of powdered potassium carbonate in 1.5 liters of acetone, and the reaction mixture is refluxed for 3 hours. After cooling, the mixture is filtered through kieselguhr and evaporated.

124.8 g of ethyl 2-cyano-2-methoximino-acetate (E isomer) are obtained as a red-brown oil of 85% purity (GC). The yield is accordingly 68% of theory. After chromatography on five times the amount of silica gel 60 using chloroform, a 93% purity pale yellow oil is obtained.

The following substituted aminal derivatives of the general formula (I) are obtained in an analogous fashion and in accordance with processes (a) and (b) according to the invention:

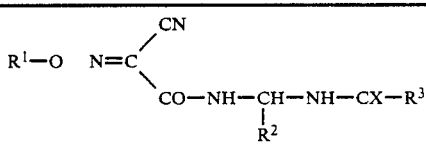

| Ex. No. | $R^1$ | $R^2$ | X | $R^3$ | Melting point (°C.) |
|---|---|---|---|---|---|
| 2 | $CH_3$ | H | O | $-C_2H_5$ | 118–20 (E-isomer) |

-continued

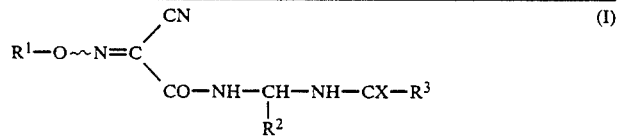
(I)

| Ex. No. | R¹ | R² | X | R³ | Melting point (°C.) |
|---|---|---|---|---|---|
| 3 | $CH_3$ | H | O | $-C_3H_7$-i | 145–47 (E-isomer) |
| 4 | $CH_3$ | H | O | —C₆H₄— (phenyl) | 165–67 (E-isomer) |
| 5 | $CH_3$ | H | O | $-OCH_3$ | 99–102 (E-isomer) |
| 6 | $CH_3$ | H | O | $-OC_2H_5$ | 76–78 (E-isomer) |
| 7 | $CH_3$ | H | O | $-NHCH_3$ | 141–42 (E-isomer) |
| 8 | $CH_3$ | H | O | $-CH_2OCH_3$ | 89–91 (E-isomer) |
| 9 | $CH_3$ | H | O | $-H$ | 130–31 (E-isomer) |
| 10 | $CH_3$ | H | O | 2-furyl | 138–39 (E-isomer) |
| 11 | $CH_3$ | H | O | $-CH_2Cl$ | 133–35 (E-isomer) |
| 12 | $CH_3$ | H | O | $-CH_2OCOCH_3$ | 111–13 (E-isomer) |
| 13 | $CH_3$ | H | O | $-CHCl_2$ | 148–50 (E-isomer) |
| 14 | $CH_3$ | H | O | $-CH_2$-phenyl | 125–27 (E-isomer) |
| 15 | $CH_3$ | H | O | cyclopropyl | 156–58 (E-isomer) |
| 16 | $CH_3$ | H | O | $-COOC_2H_5$ | 95–97 (E-isomer) |
| 17 | $CH_3$ | H | O | $-CF_3$ | 120–21 (E-isomer) |
| 18 | $CH_3$ | H | O | $-CH_2$-(1,2,4-triazol-1-yl) | 202–05 (E-isomer) |
| 19 | $CH_3$ | H | O | $-CH_2-NH-CO-O-CH_2$-phenyl | 133–35 (E-isomer) |
| 20 | $CH_3$ | H | O | $-CH_2-NH-CO-O-C(CH_3)_3$ | amorph (E-isomer) |
| 21 | $CH_3$ | H | O | $-CH_2-NH-CO-OC_2H_5$ | 119–20 (E-isomer) |

Use examples

In the following use examples, the compounds shown below are employed as comparison substances:

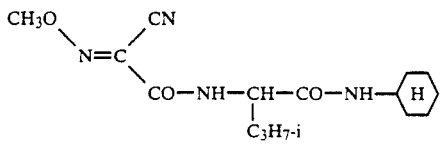
(A)

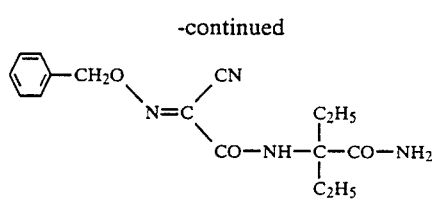
(B)

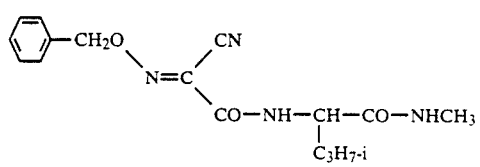
(C)

(known from DE-OS (German Published Specification) 3,521,131).

EXAMPLE A

Plasmopara test (vines)/protective
Solvent: 4.7 parts by weight of acetone
Emulsifier: 0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To text for protective activity, young plants are sprayed with the preparation of active compound until dripping wet. After the spray coating has dried on, the plants are inoculated with an aqueous spore suspension of Plasmopara viticola and then remain in a humidity chamber at 20° to 22° C. and 100% relative atmospheric humidity for 1 day. The plants are then placed in a greenhouse at 22° C. and about 80% atmospheric humidity for 5 days. The plants are then moistened and placed in a humidity chamber for 1 day.

Evaluation is carried out 7 days after the inoculation.

In this test, a clearly superior activity compared with the prior art is shown, for example, by the compounds according to preparation Examples 1, 2, 3, 4, 5, 6 and 7.

EXAMPLE B

Phytophthora Test (tomato)/protective
Solvent: 4.7 parts by weight of acetone
Emulsifier: 0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous spore suspension of Phyrophthora infestans.

The plants are placed in an incubation cabin at 100% relative atmospheric humidity and at about 20° C.

Evaluation is carried out 3 days after the inoculation.

In this test, a clearly superior activity compared with the prior art is shown, for example, by the compounds according to preparation Examples 1, 2, 3, 4, 5, 6 and 7.

It will be appreciated that the instant specification and claims are set forth by way of illustration and not limitation, and that various modifications and changes may be made without departing from the spirit and scope of the present invention.

What is claimed is:

1. An N,N'-diacylaminal of the formula

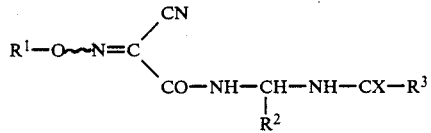

in which
$R^1$ stands for alkyl which is unsubstituted or substituted by halogen, cyano, —COOR$^I$, —CONR$^{II}$R$^{III}$, —OR$^{IV}$, acyl, optionally substituted aryl or optionally substituted cycloalkyl; or
stands for optionally substituted alkenyl, optionally substituted alkinyl, optionally substituted cycloalkyl, or optionally substituted cycloalkenyl;
$R^2$ stands for hydrogen or alkyl which is unsubstituted or substituted by cyano, alkoxy, alkylthio, —COOR$^I$, acylamino, optionally substituted aryl or optionally substituted cycloalkyl; or
stands for optionally substituted alkenyl, optionally substituted alkinyl, optionally substituted cycloalkyl, optionally substituted cycloalkenyl, or optionally substituted aryl;
$R^3$ stands for hydrogen or for alkyl which is unsubstituted or substituted by halogen, alkoxy, alkylthio, alkylsulphinyl, alkylsulphonyl, acyloxy, acylamino, cyano, —COOR$^I$, optionally substituted aryl or optionally substituted cycloalkyl; or
stands for optionally substituted alkenyl or optionally substituted alkinyl; or
stands for optionally bridged and/or fused, optionally substituted cycloalkyl or cycloalkenyl; or
stands for optionally fused, optionally substituted aryl; or for alkoxycarbonyl, —OR$^4$, —SR$^4$ or —NR$^5$R$^6$;
$R^4$ stands for alkyl which is unsubstituted or substituted by halogen, —OR$^{IV}$, —SR$^{IV}$, —COOR$^I$, —CONR$^{II}$R$^{III}$, —CN, —NR$^{II}$R$^{III}$, acyl, optionally substituted aryl, optionally substituted aryloxy, optionally substituted cycloalkyl, or optionally substituted cycloalkenyl; or
stands for optionally substituted alkenyl, optionally substituted alkinyl, optionally substituted cycloalkyl, or cycloalkenyl;
$R^5$ stands for hydrogen or for alkyl which is unsubstituted or substituted by halogen, cyano, —COOR$^I$, —CONR$^{II}$R$^{III}$, —NR$^{II}$R$^{III}$, —OR$^{IV}$, —S(OR$_n$-R$^{IV}$, acyl, or optionally substituted aryl, optionally substituted cycloalkyl, or cycloalkenyl; or
stands for optionally substituted alkenyl, optionally substituted alkinyl, optionally substituted cycloalkyl, optionally substituted cycloalkenyl, or optionally substituted aryl; and
$R^6$ stands for hydrogen or for alkyl which is unsubstituted or substituted by halogen, cyano, —COOR$^I$, —CONR$^{II}$R$^{III}$, —NR$^{II}$R$^{III}$, —OR$^{IV}$, —S(O)$_n$R$^{IV}$, acyl, or optionally substituted aryl, optionally substituted cycloalkyl, or optionally substituted cycloalkenyl; or
stands for optionally substituted alkenyl, optionally substituted alkinyl, optionally substituted cycloalkyl, optionally substituted cycloalkenyl, or optionally substituted aryl, or the —OR$^{IV}$ group;
$R^I$ stands for hydrogen or alkyl which is unsubstituted or substituted by halogen, or optionally substituted aryl, optionally substituted cycloalkyl, or optionally substituted cycloalkenyl;
$R^{II}$ and $R^{III}$ are identical or different and stand for hydrogen or alkyl which is unsubstituted or substituted by halogen, —COOR$^{IV}$, —CONR$^I$R$^{IV}$, optionally substituted aryl, optionally substituted cycloalkyl, or optionally substituted cryloalkenyl; or stand for alkenyl, alkinyl, optionally substituted cycloalkyl, optionally substituted cycloalkenyl, or optionally substituted aryl;
$R^{IV}$ stands for hydrogen, alkyl, aralkyl, or acyl;
n stands for the numbers 0, 1, or 2; and
X stands for oxygen or sulfur;

wherein the term "optionally substituted aryl" stands for phenyl which is unsubstituted or substituted by one or more substituents independently selected from the group consisting of halogen, alkyl and alkoxy each having 1 to 4 carbon atoms, halogenoalkyl and halogenoalkoxy each having 1 to 2 different carbon atoms and 1 to 5 identical or different halogen atoms;

the term "optionally substituted aryloxy" stands for "optionally substituted aryl" bonded through oxygen;

the terms "optionally substituted cycloalkyl" and "optionally substituted cycloalkenyl" stand for cycloalkyl and cycloalkenyl which are each unsubstituted or substituted by alkyl having 1 to 4 carbon atoms;

the terms "optionally substituted alkenyl" and "optionally substituted alkinyl" stand for alkenyl or alkinyl which are each unsubstituted or substituted by phenyl which is unsubstituted or substituted by a substituent selected from the group consisting of halogen and alkyl having 1 to 4 carbon atoms;

the term "optionally bridged and/or fused optionally substituted cycloalkyl or cycloalkenyl" stands for cycloalkyl or cycloalkenyl each of which is (1) unbridged or bridged by methylene or ethylene, (2) unfused or fused to 1 or 2 benzene, cyclopentane, or cyclohexane rings, and (3) unsubstituted or substituted by one or more substituents independently selected from the group consisting of halogen, alkyl and alkoxy each having 1 to 4 carbon atoms, acyloxy and acylamino each having 2 to 5 carbon atoms, the oxo group, phenyl, hydroxycarbonyl, and alkoxycarbonyl having 1 to 4 carbon atoms in the alkoxy part; and the term "optionally fused, optionally substituted aryl" stands for phenyl which is (1) unfused or fused to 1 to 2 benzene or cyclohexane rings and (2) unsubstituted or substituted by one or more substituents independently selected from the group consisting of halogen, hydroxyl, nitro, alkyl and alkoxy each having 1 to 4 carbon atoms, halogenoalkyl and halogenoalkoxy each having 1 to 2 carbon atoms and 2 to 5 identical or different halogen atoms, acylamino and acylalkylamino each having 2 to 5 carbon atoms in the acyl part and 1 to 4 carbon atoms in the alkyl part, hydroxycarbonyl and alkoxycarbonyl having 1 to 4 carbon atoms in the alkoxy part.

2. An N,N'-diacylaminal according to claim 1, in which $R^1$ stands for straight-chain or branched alkyl having 1 to 6 carbon atoms which is unsubstituted or monosubstituted to pentasubstituted by identical or different substituents selected from the group consisting of (i) fluorine, chlorine, bromine, iodine, cyano, —COOR$^I$, —CONR$^{II}$R$^{III}$, —OR$^{IV}$, acyl having 2 to 9 carbon atoms, phenyl which is unsubstituted or monosubstituted to pentasubstituted by identical or different substituents selected from the group consisting of (ii) halogen, alkyl and alkoxy each having 1 to 4 carbon atoms, halogenoalkyl and halogenoalkoxy each having 1 to 2 carbon atoms and 1 to 5 identical or different halogen atoms; or (i) cycloalkyl having 3 to 6 carbon atoms which is unsubstituted or monosubstituted to pentasubstituted by identical or different (ii) alkyl having 1 to 4 carbon atoms;

$R^2$ stands for hydrogen or straight-chain or branched alkyl having 1 to 5 carbon atoms which is unsubstituted or monosubstituted to pentasubstituted by identical or different substituents (i) selected from the group consisting of cyano, alkoxy and alkylthio, each having 1 to 4 carbon atoms, —COOR$^1$, acylamino having 2 to 9 carbon atoms, phenyl which is unsubstituted or monosubstituted to pentasubstituted by identical or different substituents (ii) halogen, alkyl and alkoxy each having 1 to 4 carbon atoms, halogenoalkyl and halogenoalkoxy each having 1 or 2 carbon atoms and 1 to 5 identical or different halogen atoms, and (i) cycloalkyl having 3 to 6 carbon atoms which is unsubstituted or monosubstituted to pentasubstituted by identical or different (ii) alkyl having 1 to 4 carbon atoms; or stands for phenyl which is unsubstituted or monosubstituted to pentasubstituted by identical substituents (i) halogen, alkyl and alkoxy each having 1 to 4 carbon atoms, halogenoalkyl and halogenoalkoxy each having 1 or 2 carbon atoms and 1 to 5 identical or different halogen atoms;

$R^3$ stands for hydrogen or straight-chain or branched alkyl having 1 to 6 carbon atoms which is unsubstituted or monosubstituted to pentasubstituted by identical or different substituents (i) selected from the group consisting of fluorine, chlorine, bromine, iodine, cyano, alkoxy, alkylthio, alkylsulphinyl and alkylsulphonyl each having 1 to 4 carbon atoms, acyloxy and acylamino each having 2 to 9 carbon atoms, —COOR$^I$, phenyl which is unsubstituted or monosubstituted to pentasubstituted by identical or different substituents (ii) halogen, alkyl and alkoxy each having 1 to 4 carbon atoms, halogenoalkyl and halogenoalkoxy each having 1 or 2 carbon atoms and 1 to 5 identical or different halogen atoms, or (i) cycloalkyl having 3 to 6 carbon atoms which is unsubstituted on monosubstituted to pentasubstituted by identical or different (ii) alkyl having 1 to 4 carbon atoms; or stands for cycloalkyl having 3 to 6 carbon atoms or cycloalkenyl having 5 to 7 carbon atoms, each of which is unbridged or bridged by methylene or ethylene, unfused or fused to 1 or 2 benzene, cyclopentane or cyclohexane rings, and unsubstituted or monosubstituted to pentasubstituted by identical or different substituents (i) selected from the group consisting of halogen, alkyl and alkoxy each having 1 to 4 carbon atoms, acyloxy and acylamino each having 2 to 5 carbon atoms, the oxo group, phenyl, hydroxycarbonyl and alkoxycarbonyl having 1 to 4 carbon atoms in the alkoxy part; or stands for phenyl which is unfused or fused to 1 or 2 benzene or cyclohexane rings and unsubstituted or monosubstituted to pentasubstituted by identical or different substituents (i) selected from the group consisting of halogen, hydroxyl, nitro, alkyl and alkoxy each having 1 to 4 carbon atoms, halogenoalkyl and halogenoalkoxy each having 1 or 2 carbon atoms and 2 to 5 identical or different halogen atoms, acylamino and acylalkylamino each having 2 to 5 carbon atoms in the acyl part and 1 to 4 carbon atoms in the alkyl part, hydroxycarbonyl, and alkoxycarbonyl having 1 to 4 carbon atoms in the alkoxy part, or stands for alkoxycarbonyl having 1 to 4 carbon atoms in the alkoxy part, or for —OR$^4$, —SR$^4$ or —NR$^5$R$^6$; or R$^1$, R$^2$ and R$^3$ independently of one another stand for straight-chain or branched alkenyl or alkinyl, each of which has 2 to 6 carbon atoms is unsubstituted or monosubstituted to trisubstituted by identical or different substituents selected from the group consisting of (i) phenyl which is unsubstituted or monosubstituted to pentasubstituted by identical or different substituents selected from the group consisting of (ii) halogen and alkyl having 1 to 4 carbon atoms;

X stands for oxygen or sulfur;

wherein

R$^4$ stands for straight-chain or branched alkyl having 1 to 6 carbon atoms which is unsubstituted or monosubstituted to pentasubstituted by identical or different substituents (i) selected from the group consisting of halogen, —OR$^{IV}$, —SR$^{IV}$, —COOR$^I$, —CONR$^{II}$R$^{III}$, CN, —NR$^{II}$R$^{III}$, acyl having 2 to 9 carbon atoms, phenyl or phenoxy, each of which is unsubstituted or monosubstituted to pentasubstituted by identical or different substituents (ii) selected from the group consisting of halogen and alkyl having 1 to 4 carbon atoms, and (i) cycloalkyl having 3 to 6 carbon atoms or cycloalkenyl having 5 to 7 carbon atoms, each of which is unsubstituted or monosubstituted to pentasubstituted by identical or different (ii) alkyl having 1 to 4 carbon atoms; or stands for alkenyl or alkinyl each having 2 to 6 carbon atoms, or for cycloalkyl having 3 to 6 carbon atoms or cycloalkenyl having 5 to 7 carbon atoms, each of which is unsubstituted or monosubstituted to pentasubstituted by identical or different (i) alkyl having 1 to 4 carbon atoms;

R$^5$ stands for hydrogen or for straight-chain or branched alkyl having 1 to 4 carbon atoms which is unsubstituted or monosubstituted or disubstituted by identical or different substituents (i) selected from the group consisting of halogen, —cyano, —COOR$^I$, —CONR$^{II}$R$^{III}$, —NR$^{II}$R$^{III}$, —OR$^{IV}$, —S(O)$_n$R$^{IV}$, acyl having 2 to 9 carbon atoms, phenyl, which is unsubstituted or monosubstituted to pentasubstituted by identical or different substituents (ii) selected from the group consisting of halogen and alkyl having 1 to 4 carbon atoms, and (i) cycloalkyl having 3 to 6 carbon atoms or cycloalkenyl having 5 to 7 carbon atoms, each of which is unsubstituted or monosubstituted to pentasubstituted by identical or different (ii) alkyl having 1 to 4 carbon atoms; or stands for straight-chain or branched alkenyl or alkinyl each having 2 to 6 carbon atoms, for cycloalkenyl having 5 to 7 carbon atoms, which is unsubstituted or monosubstituted to pentasubstituted by identical or different (i) alkyl having 1 to 4 carbon atoms; or for cycloalkyl having 3 to 6 carbon atoms which is unsubstituted or monosubstituted to pentasubstituted by identical or different substituents (i) from the group consisting of halogen, alkyl and alkoxy each having 1 to 4 carbon atoms, cyano, amino, carbamoyl, alkylamino, dialkylamino, alkylcarbamoyl and dialkylcarbamoyl each having 1 to 4 carbon atoms in each alkyl part, alkoxycarbonylamino having 1 to 4 carbon atoms in the alkoxy part, cycloalkyl and cycloalkylalkyl having 5 or 6 carbon atoms in the cycloalkyl part and 1 to 4 carbon atoms in the straight-chain or branched alkyl part, or phenyl which is optionally unsubstituted or monosubstituted to pentasubstituted by identical or different substituents (ii) from the group consisting of halogen and alkyl having 1 to 4 carbon atoms; or stands for phenyl which is unsubstituted or monosubstituted to pentasubstituted by identical or different substituents (i) from the group consisting of halogen, alkyl or alkoxy each having 1 to 4 carbon atoms, or halogenoalkyl or halogenalkoxy each having 1 or 2 carbon atoms and 1 to 5 identical or different halogen atoms;

R$^6$ stands for the meanings of R$^5$ or the —OR$^{IV}$ group;

wherein

R$^I$ stands for hydrogen or straight-chain or branched alkyl having 1 to 6 carbon atoms;

R$^{II}$ and R$^{III}$ independently of one another stand for hydrogen, straight-chain or branched alkyl having 1 to 6 carbon atoms, phenylalkyl which has 1 to 4 carbon atoms in the straight-chain or branched alkyl part and is unsubstituted or monosubstituted to pentasubstituted on the phenyl by identical or different substituents (i) selected from the group consisting of halogen, alkyl or alkoxy each having 1 to 4 carbon atoms, or halogenoalkyl or halogenoalkoxy each having 1 or 2 carbon atoms and 2 to 5 identical or different halogen atoms; or stand for alkoxycarbonylalkyl, carbamoylalkyl, alkylcarbamoylalkyl or dialkylcarbonylalkyl each having 1 to 4 carbon atoms in each alkyl part, or for cycloalkyl having 3 to 6 carbon atoms which is unsubstituted or substituted by straight-chain or branched (i) alkyl having 1 to 4 carbon atoms;

R$^{IV}$ stands for hydrogen, straight-chain or branched alkyl having 1 to 6 carbon atoms, phenylalkyl which has 1 to 4 carbon atoms in the straight-chain or branched alkyl part and is unsubstituted or monosubstituted to pentasubstituted on the phenyl by identical or different substituents (i) selected from the group consisting of halogen, alkyl or alkoxy each having 1 to 4 carbon atoms, or halogenoalkyl or halogenoalkoxy each having 1 or 2 carbon atoms and 2 to 5 identical or different halogen atoms; or stands for acyl having 2 to 9 carbon atoms; and n stands for the numbers 0, 1 or 2.

3. An N,N'-diacylaminal according to claim 1, in which stands for straight-chain or branched alkyl having 1 to 4 carbon atoms which is unsubstituted or monosubstituted to trisubstituted by identical or different substituents (i) selected from the group consisting of fluorine, chlorine, bromine, iodine, cyano, —COOR$^I$, —CONR$^{II}$RIII, —OR$^{IV}$, acyl having 2 to 9 carbon atoms, phenyl which is unsubstituted or monosubstitited to trisubstituted by identical or different substituents (ii) selected from the group consisting of fluorine, chlorine, methyl and methoxy; or (i) cyclopropyl or cyclohexyl, each of which is unsubstituted or monosubstituted to trisubstituted by (ii) methyl; or stands for allyl or propargyl each of which is unsubstituted or monosubstituted or disubstituted by methyl;

$R^2$ stands for hydrogen or straight-chain or branched alkyl having 1 to 4 carbon atoms which is unsubstituted or monosubstituted to trisubstituted by identical or different substituents (i) selected from the group consisting of cyano, methoxy, ethoxy, methylthio, ethylthio, —COOR$^I$, acylamino having 2 to 9 carbon atoms, phenyl which is unsubstituted or monosubstituted to trisubstituted by identical or different substituents (ii) from the group consisting of halogen, methyl, or methoxy, or (i) cyclopropyl or cyclohexyl, each of which is unsubstituted or monosubstituted to trisubstituted by (ii) methyl; or stands for allyl, allenyl, vinyl, propargyl or ethinyl, each of which is unsubstituted or substituted by (i) phenyl which is unsubstituted or monosubstituted to trisubstituted by identical or different substituents (ii) from the group consisting of halogen and methyl; or stands for phenyl which is unsubstituted or monosubstituted to trisubstituted by identical substituents (i) from the group consisting of halogen, methyl, and methoxy;

$R^3$ stands for hydrogen or straight-chain or branched alkyl having 1 to 4 carbon atoms which is unsubstituted or monosubstituted to trisubstituted by identical or different substituents (i) selected from the group consisting of fluorine, chlorine, bromine, iodine, cyano, alkoxy, alkylthio, alkylsulphinyl and alkylsulphonyl each having 1 or 2 carbon atoms, acyloxy and acylamino each having 2 to 9 carbon atoms, —COOR$^I$, cyclopropyl, cyclopentyl, cyclohexyl or phenyl which is unsubstituted or monosubstituted to trisubstituted by identical or different substituents (ii) from the group consisting of halogen and methyl; or stands for vinyl or ethinyl, each of which is unsubstituted or substituted by (i) phenyl which is unsubstituted or monosubstituted to trisubstituted by identical or different substituents (ii) from the group consisting of halogen and methyl, or by (i) methyl; or stands for cyclopropyl, cyclopentyl, cyclohexyl, cyclopentenyl, or cyclohexenyl, each of which is unbridged or bridged by methylene or ethylene, unfused or fused to 1 or 2 benzene, cyclopentane or cyclohexane rings, and unsubstituted or monosubstituted to trisubstituted by identical or different substituents (i) selected from the group consisting of halogen, methyl, methoxy, acyloxy and acylamino each having 2 to 5 carbon atoms, the oxo group, phenyl, hydroxycarbonyl, methoxycarbonyl and ethoxycarbonyl; or stands for phenyl which is unfused or fused to 1 or 2 benzene or cyclohexane rings and unsubstituted or monosubstituted to trisubstituted by identical or different substituents (i) selected from the group consisting of fluorine, chlorine, hydroxyl, nitro, methyl, methoxy, acylamino and N-alkylacylamino each having 2 to 5 carbon atoms in the acyl part and 1 or 2 carbon atoms in the alkoxy part, hydroxycarbonyl, methoxycarbonyl and ethoxycarbonyl; or stands for alkoxycarbonyl having 1 to 4 carbon atoms in the alkoxy part, or for —OR$^4$, —SR$^4$ or —NR$^5$R$^6$;

X stands for oxygen or sulfur;
wherein $R^4$ stands for straight-chain or branched alkyl having 1 to 4 carbon atoms which is unsubstituted or monosubstituted to trisubstituted by identical or different substituents (i) selected from the group consisting of fluorine, chlorine, —OR$^{IV}$, —SR$^{IV}$, —COOR$^I$, —CONR$^{II}$R$^{III}$, CN, —NR$^{II}$R$^{III}$, alkylcarbonyl having 1 to 4 carbon atoms in the straight-chain or branched alkyl part, phenyl or phenoxy, each of which is unsubstituted or monosubstituted to trisubstituted by identical or different substituents (ii) selected from the group consisting of halogen and methyl, or (i) cyclopropyl, cyclohexyl, cyclopentenyl or cyclohexenyl, each of which is unsubstituted or monosubstituted to trisubstituted by (ii) methyl; or stands for allyl or propargyl, each of which is unsubstituted or monosubstituted or disubstituted by (i) methyl; or for cyclopropyl, cyclohexyl, cyclopentenyl or cyclohexenyl, each of which is unsubstituted or monosubstituted to trisubstituted by (ii) methyl;

$R^5$ stands for hydrogen or for straight-chain or branched alkyl having 1 to 4 carbon atoms which is unsubstituted or monosubstituted or disubstituted by identical or different substituents (i) selected from the group consisting of halogen, cyano, —COOR$^I$, —CONR$^{II}$R$^{III}$, CN, —NR$^{II}$R$^{III}$, OR$^{IV}$, —S(O)$_n$R$^{IV}$, acyl having 2 to 9 carbon atoms, phenyl, which is unsubstituted or monosubstituted to trisubstituted by identical or different substituents (ii) selected from the group consisting of halogen and alkyl having 1 to 4 carbon atoms, or (i) cycloalkyl having 3 to 6 carbon atoms or cycloalkenyl having 5 to 7 carbon atoms, each of which is unsubstituted or substituted by (ii) straight-chain or branched alkyl having 1 to 4 carbon atoms; or stands for straight-chain or branched alkenyl or alkinyl each having 2 to 6 carbon atoms, for cycloalkenyl having 5 to 7 carbon atoms, which is unsubstituted or substituted by straight-chain or branched (i) alkyl having 1 to 4 carbon atoms; or for cycloalkyl having 3 to 6 carbon atoms which is unsubstituted or substituted by (i) halogen, straight-chain or branched alkyl and alkoxy each having 1 to 4 carbon atoms, cyano, amino, carbamoyl, in each case straight-chain or branched alkylamino, dialkylamino, alkylcarbamoyl and dialkylcarbamoyl each having 1 to 4 carbon atoms in each alkyl part, alkoxycarbonylamino having 1 to 4 carbon atoms in the straight-chain or branched alkoxy part, cycloalkyl and cycloalkylalkyl having 5 or 6 carbon atoms in the cycloalkyl part and 1 to 4 carbon atoms in the straight-chain or branched alkyl part, or phenyl, which is unsubstituted or monosubstituted to trisubstituted by identical or different substituents (ii) from the group consisting of halogen and alkyl having 1 to 4 carbon atoms; or stands for phenyl which is unsubstituted or monosubstituted to trisubstituted by identical or different substituents (i) from the group consisting of halogen, straight-chain or branched alkyl or alkoxy each having 1 to 4 carbon atoms, or halogenoalkyl or halogenalkoxy each having 1 or 2 carbon atoms and 1 to 5 identical or different halogen atoms;

$R^6$ stands for the meanings of $R^5$ or the —$OR^{IV}$ group;

wherein $R^I$ stands for hydrogen or straight-chain or branched alkyl having 1 to 4 carbon atoms;

$R^{II}$ and $R^{III}$ independently of one another stand for hydrogen, straight-chain or branched alkyl having 1 to 4 carbon atoms, or benzyl or phenethyl each of which is unsubstituted or monosubstituted to trisubstituted on the phenyl by identical or different substituents (i) selected from the group consisting of fluorine, chlorine, methyl, methoxy and trifluoromethyl; or stand for alkoxycarbonylalkyl having 1 to 4 carbon atoms in the alkoxy part and 1 or 2 carbon atoms in the alkyl part, carbamoylalkyl, alkylcarbamoylalkyl or dialkylcarbonylalkyl each having 1 or 2 carbon atoms in each alkyl part, or for cycloalkyl having 3 to 6 carbon atoms which is unsubstituted or monosubstituted to trisubstituted by identical or different substituents selected from the group consisting of methyl and ethyl;

$R^{IV}$ stands for hydrogen, straight-chain or branched alkyl having 1 to 4 carbon atoms, or benzyl or phenethyl each of which is unsubstituted or monosubstituted to trisubstituted on the phenyl by identical or different substituents selected from the group consisting of fluorine, chlorine, methyl, methoxy and trifluoromethyl; or stands for acyl having 2 to 9 carbon atoms; and n stands for the numbers 0, 1 or 2.

4. An N,N'-diacylaminal according to claim 1, in which $R^1$ stands for straight-chain or branched alkyl having 1 or 2 carbon atoms which is unsubstituted or monosubstituted to trisubstituted by identical or different substituents selected from the group consisting of (i) fluorine, chlorine, cyano, —$COOR^I$, —$CONR^{II}R^{III}$, —$OR^{IV}$, alkylcarbonyl having 1 to 4 carbon atoms in the straight-chain or branched alkyl part, phenyl which is unsubstituted or monosubstitited to trisubstituted by identical or different substituents (ii) selected from the group consisting of fluorine, chlorine and methyl; or (i) cyclopropyl or cyclohexyl, each of which is unsubstituted or monosubstituted to trisubstituted by (ii) methyl; or stands for allyl or propargyl;

$R^2$ stands for hydrogen or for alkyl having 1 to 4 carbon atoms which is unsubstituted or monosubstituted or disubstituted by identical or different substituents (i) selected from the group consisting of cyano, methoxy, ethoxy, methylthio, ethylthio, —$COOR^I$, alkylcarbonylamino having 1 to 4 carbon atoms in the straight-chain or branched alkyl part, phenyl which is unsubstituted or monosubstituted to trisubstituted by identical or different substituents (ii) from the group consisting of halogen, methyl, or methoxy, or (i) cyclopropyl or cyclohexyl, each of which is unsubstituted or monosubstituted to trisubstituted by (ii) methyl; or stands for allyl, allenyl, vinyl, propargyl or ethinyl, each of which is unsubstituted or substituted by (i) phenyl which may be unsubstituted or monosubstituted to trisubstituted by identical or different substituents (ii) from the group consisting of halogen and methyl; or stands for phenyl which is unsubstituted or monosubstituted to trisubstituted by identical substituents (i) from the group consisting of halogen, methyl, and methoxy;

$R^3$ stands for hydrogen or straight-chain or branched alkyl having 1 to 4 carbon atoms which is unsubstituted or monosubstituted or disubstituted by identical or different substituents (i) selected from the group consisting of fluorine, chlorine, bromine, iodine, cyano, alkoxy, alkylthio, alkylsulphinyl and alkylsulphonyl each having 1 or 2 carbon atoms, alkylcarbonyloxy having 1 to 4 carbon atoms in the straight-chain or branched alkyl part, formamido, alkylcarbonylamino having 1 or 2 carbon atoms in the alkyl part, which is unsubstituted or substituted by (ii) fluorine, (i) benzoylamino which is unsubstituted or substituted by (ii) chlorine, (i) alkoxycarbonylamino having 1 to 4 atoms in the straight-chain or branched alkoxy part, —$COOR^I$, cyclopropyl, cyclopentyl, cyclohexyl or phenyl which is unsubstituted or monosubstituted to trisubstituted by identical or different substituents (ii) from the group consisting of halogen and methyl; or stands for vinyl or ethinyl, each of which is unsubstituted or monosubstituted or disubstituted by identical or different substituents selected from the group consisting of (i) phenyl which is unsubstituted or monosubstituted to trisubstituted by identical or different substituents (ii) from the group consisting of halogen and methyl, or by (i) methyl; or stands for cyclopropyl, cyclopentyl, cyclohexyl, cyclopentenyl, or cyclohexenyl, each of which is unbridged or bridged by methylene or ethylene, unfused or fused to 1 or 2 benzene, cyclopentane or cyclohexane rings, and unsubstituted or monosubstituted to trisubstituted by identical or different substituents (i) selected from the group consisting of halogen, methyl, the oxo group, phenyl, hydroxycarbonyl, methoxycarbonyl and ethoxycarbonyl; or stands for phenyl which is unfused or fused to 1 or 2 benzene or cyclohexane rings and is unsubstituted or monosubstituted to trisubstituted by identical or different substituents (i) selected from the group consisting of fluorine, chlorine, hydroxyl, nitro, methyl, methoxy, acetoxy, acetamido, hydroxycarbonyl, methoxycarbonyl and ethoxycarbonyl; or stands for alkoxycarbonyl having 1 to 4 carbon atoms in the alkoxy part, or for —$OR^4$, —$SR^4$ or —$NR^5R^6$;

X stands for oxygen or sulfur;

wherein $R^4$ stands for straight-chain or branched alkyl having 1 or 2 carbon atoms which is unsubstituted or monosubstituted or disubstituted by identical or different substituents (i) selected from the group consisting of fluorine, chlorine, methoxy, ethoxy, methylthio, alkoxycarbonyl having 1 to 4 carbon atoms in the straight-chain or branched alkoxy part, carbamoyl, methylcarbamoyl, dimethylcarbamoyl, cyano, dimethylamino, diethylamino, acetyl, pivaloyl, or phenyl or phenoxy, each of which is unsubstituted or monosubstituted to trisubstituted by identical or different substituents (ii) selected from the group consisting of halogen and methyl, or (i) cyclopropyl or cyclohexyl, each of which is unsubstituted or monosubstituted to trisubstituted by (ii) methyl; or stands for allyl or propargyl, each of which is unsubstituted or monosubstituted or disubstituted by (i) methyl; or for cyclohexyl which is unsubstituted or monosubstituted to trisubstituted by (i) methyl;

$R^5$ stands for hydrogen or for straight-chain or branched alkyl having 1 to 4 carbon atoms or alkyl having 1 to 3 carbon atoms which is monosubstituted or disubstituted by identical or different substituents (i) selected from the group consisting of chlorine, hydroxyl, alkylcarbonyloxy having 1 to 4 carbon atoms in the straight-chain or branched alkyl part, alkylcarbonyl having 1 to 4 carbon atoms in the straight-chain or branched alkyl part, alkoxy and alkylthio each having 1 or 2 carbon atoms, alkoxycarbonyl having 1 to 4 carbon atoms in the straight-chain or branched alkoxy part, carbamoyl, methylcarbamoyl, dimethylcarbamoyl, cyano, dimethylamino, diethylamino, cyclopropyl, cyclohexyl or phenyl, which is unsubstituted or monosubstituted to trisubstituted by identical or different substituents (ii) selected from the group consisting of chlorine and methyl; or stands for allyl or propargyl, for 1-cyclohexenyl, or for cyclohexyl which is unsubstituted or monosubstituted to trisubstituted by identical or different substituents (i) from the group consisting of chlorine, methyl, ethyl, methoxy, cyano, amino, alkylamino, dialkylamino, alkylcarbamoyl and dialkylcarbamoyl each having 1 or 2 carbon atoms in each alkyl part, cyclohexyl or cyclohexylalkyl having 1 or 2 carbon atoms in the alkyl part; or stands for phenyl which is unsubstituted or monosubstituted to trisubstituted by identical or different substituents (i) from the group consisting of chlorine and methyl;

$R^6$ stands for the meanings of $R^5$ or the $-OR^{IV}$ group;

wherein $R^I$ stands for methyl, ethyl, n- or i-propyl and n-, i-, s- or t-butyl;

$R^{II}$ and $R^{III}$ independently of one another stand for hydrogen, methyl, ethyl, n- or i-propyl, for benzyl which is unsubstituted or monosubstituted to trisubstituted on the phenyl by identical or different substituents (i) selected from the group consisting of chlorine and methyl; or stand for alkoxycarbonylalkyl having 1 or 2 carbon atoms in the alkoxy part and 1 or 2 carbon atoms in the alkyl part, carbamoylalkyl, alkylcarbamoylalkyl or dialkylcarbonylalkyl each having 1 or 2 carbon atoms in each alkyl part, or for cyclohexyl which is unsubstituted or monosubstituted to trisubstituted by (i) methyl; and $R^{IV}$ stands for hydrogen, alkyl having 1 or 2 carbon atoms, or benzyl which is unsubstituted or monosubstituted to trisubstituted on the phenyl by identical or different substituents (i) selected from the group consisting of fluorine, chlorine, and methyl.

5. An N-(2-cyano-2-oximino-acetyl)-aminal of the formula

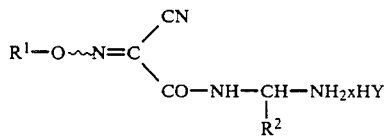

in which
$R^1$ stands for alkyl which is unsubstituted or substituted by halogen, cyano, $-COOR^I$, $-CONR^{II}R^{III}$, $-OR^{IV}$, acyl, optionally substituted aryl or optionally substituted cycloalkyl; or
stands for optionally substituted alkenyl, optionally substituted alkinyl, optionally substituted cycloalkyl, or optionally substituted cycloalkenyl;

$R^2$ stands for hydrogen or alkyl which is unsubstituted or substituted by cyano, alkoxy, alkylthio, $-COOR^I$, acylamino, optionally substituted aryl or optionally substituted cycloalkyl; or
stands for optionally substituted alkenyl, optionally substituted alkinyl, optionally substituted cycloalkyl, optionally substituted cycloalkenyl, or optionally substituted aryl;

$R^I$ stands for hydrogen or alkyl which is unsubstituted or substituted by halogen, or optionally substituted aryl, optionally substituted cycloalkyl, or optionally substituted cycloalkenyl;

$R^{II}$ and $R^{III}$ are identical or different and stand for hydrogen or alkyl which is unsubstituted or substituted by halogen, $-COOR^{IV}$, $-CONR^IR^{IV}$, optionally substituted aryl, optionally substituted cycloalkyl, or optionally substituted cycloalkenyl; or stand for alkenyl, alkinyl, optionally substituted cycloalkyl, optionally substituted cycloalkenyl, or optionally substituted aryl;

$R^{IV}$ stands for hydrogen, alkyl, aralkyl, or acyl; and

HY stands for the equivalent of an inorganic or organic acid;

wherein
the term "optionally substituted aryl" stands for phenyl which is unsubstituted or substituted by one or more substituents independently selected from the group consisting of halogen, alkyl and alkoxy each having 1 to 4 carbon atoms, halogenoalkyl and halogenoalkoxy each having 1 or 2 different carbon atoms and 1 to 5 identical or different halogen atoms;

the terms "optionally substituted cycloalkyl" and "optionally substituted cycloalkenyl" stand for cycloalkyl and cycloalkenyl which are each unsubstituted or substituted by alkyl having 1 to 4 carbon atoms; and the terms "optionally substituted alkenyl" and "optionally substituted alkinyl" stand for alkenyl or alkinyl which are each unsubstituted or substituted by phenyl which is unsubstituted or substituted by a substituent selected from the group consisting of halogen and alkyl having 1 to 4 carbon atoms.

6. An isocyanate of the formula

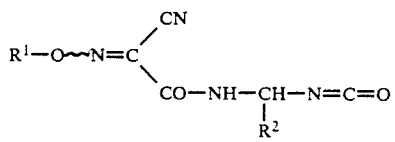

in which
- $R^1$ stands for alkyl which is unsubstituted or substituted by halogen, cyano, —COOR$^I$, —CONR$^{II}$R$^{III}$, —OR$^{IV}$, acyl, optionally substituted aryl or optionally substituted cycloalkyl; or
  stands for optionally substituted alkenyl, optionally substituted alkinyl, optionally substituted cycloalkyl, or optionally substituted cycloalkenyl;
- $R^2$ stands for hydrogen or alkyl which is unsubstituted or substituted by cyano, alkoxy, alkylthio, —COOR$^I$, acylamino, optionally substituted aryl or optionally substituted cycloalkyl; or
  stands for optionally substituted alkenyl, optionally substituted alkinyl, optionally substituted cycloalkyl, optionally substituted cycloalkenyl, or optionally substituted aryl;
- $R^I$ stands for hydrogen or alkyl which is unsubstituted or substituted by halogen, or optionally substituted aryl, optionally substituted cycloalkyl, or optionally substituted cycloalkenyl;
- $R^{II}$ and $R^{III}$ are identical or different and stand for hydrogen or alkyl which is unsubstituted or substituted by halogen, —COOR$^{IV}$, —CONR$^I$R$^{IV}$, optionally substituted aryl, optionally substituted cycloalkyl, or optionally substituted cycloalkenyl; or
  stand for alkenyl, alkinyl, optionally substituted cycloalkyl, optionally substituted cycloalkenyl, or optionally substituted aryl;
- $R^{IV}$ stands for hydrogen, alkyl, aralkyl, or acyl;

wherein
- the term "optionally substituted aryl" stands for phenyl which is unsubstituted or substituted by one or more substituents independently selected from the group consisting of halogen, alkyl and alkoxy each having 1 to 4 carbon atoms, halogenoalkyl and halogenoalkoxy each having 1 or 2 different carbon atoms and 1 to 5 identical or different halogen atoms;
- the terms "optionally substituted cycloalkyl" and "optionally substituted cycloalkenyl" stand for cycloalkyl and cycloalkenyl which are each unsubstituted or substituted by alkyl having 1 to 4 carbon atoms; and
- the terms "optionally substituted alkenyl" and "optionally substituted alkinyl" stands for alkenyl or alkinyl which are each unsubstituted or substituted by phenyl which is unsubstituted or substituted by a substituent selected from the group consisting of halogen and alkyl having 1 to 4 carbon atoms.

7. A compound according to clam 1, wherein such compound is N-acetamidomethyl-(E)-2-cyano-2-methoximinoacetamide of the formula $$CH_3O\setminus N=C / CN \atop \underset{\parallel}{C}-NH-CH_2-NH-\underset{\parallel}{C}-CH_3.$$
$$\phantom{CH_3O\setminus N=C}O\phantom{-NH-CH_2-NH-}O$$

8. A compound according to claim 1, wherein such compound is N-propionylamidomethyl-(E)-2-cyano-2-methoximinoacetamide of the formula $$CH_3O\setminus N=C / CN \atop \underset{\parallel}{C}-NH-CH_2-NH-\underset{\parallel}{C}-C_2H_5.$$

9. A compound according to claim 1, wherein such compound is N-benzoylamidomethyl-(E)-2-cyano-2-methoximinoacetamide of the formula $$CH_3O\setminus N=C / CN \atop \underset{\parallel}{C}-NH-CH_2-NH-\underset{\parallel}{C}-C_6H_5.$$

10. A compound according to claim 1, wherein such compound is N-methoxycarbonylamidomethyl-(E)-2-cyanomethoximinoacetamide of the formula $$CH_3O\setminus N=C / CN \atop \underset{\parallel}{C}-NH-CH_2-NH-\underset{\parallel}{C}-OCH_3.$$

11. A compound according to claim 1, wherein such compound is N-ethoxycarbonylamidomethyl-(E)-2-cyanomethoximinoacetamide of the formula $$CH_3O\setminus N=C / CN \atop \underset{\parallel}{C}-NH-CH_2-NH-\underset{\parallel}{C}-OC_2H_5$$

12. A fungicidal composition comprising a fungicidally effective amount of a compound according to claim 1 and a diluent.

13. A method of combating fungi which comprises applying to such fungi or to a fungus habitat a fungicidally effective amount of a cmpound according to claim 1.

14. The method according to claim 13, wherein such compound is
N-acetamidomethyl-(E)-2-cyano-2-methoximinoacetamide,
N-propionylamidomethyl-(E)-2-cyano-2-methoximinoacetamide,
N-benzoylamidomethyl-(E)-2-cyano-2-methoximinoacetamide,
N-methoxycarbonylamidomethyl-(E)-2-cyanomethoximinoacetamide, or
N-ethoxycarbonylamidomethyl-(E)-2-cyanomethoximinoacetamide.

* * * * *

UNITED STATES PATENT AND TRADEMARK OFFICE
CERTIFICATE OF CORRECTION

PATENT NO. : 4,945,111

DATED : July 31, 1990

INVENTOR(S) : Lunkenheimer et al.

It is certified that error appears in the above-identified patent and that said Letters Patent is hereby corrected as shown below:

Col. 42, line 37   Delete " $-S(OR_{n-}$ " and substitute -- $-S(O)_n R$ --

Col. 42, line 62   Delete " crycloalkenyl " and substitute -- cycloalkenyl --

Col. 43, line 40   Delete second " to " and substitute -- or --

Col. 44, line 4    Delete " 5 " and substitute -- 6 --

Col. 44, line 40   Delete " on " and substitute -- or --

Col. 46, line 52   After & under " which " insert -- $R^1$ --

Col. 50, line 16   After " 4 " insert -- carbon --

Signed and Sealed this

Sixteenth Day of June, 1992

Attest:

DOUGLAS B. COMER

*Attesting Officer*   *Acting Commissioner of Patents and Trademarks*